(12) United States Patent
Takahashi et al.

(10) Patent No.: US 8,398,543 B2
(45) Date of Patent: Mar. 19, 2013

(54) CAPSULE ENDOSCOPE ACTIVATION SYSTEM

(75) Inventors: Masaki Takahashi, Hachioji (JP); Hironao Kawano, Machida (JP)

(73) Assignee: Olympus Medical Systems Corp., Tokyo (JP)

( * ) Notice: Subject to any disclaimer, the term of this patent is extended or adjusted under 35 U.S.C. 154(b) by 9 days.

(21) Appl. No.: 13/210,822

(22) Filed: Aug. 16, 2011

(65) Prior Publication Data

US 2012/0101333 A1 Apr. 26, 2012

Related U.S. Application Data

(63) Continuation of application No. PCT/JP2011/051270, filed on Jan. 25, 2011.

(30) Foreign Application Priority Data

Mar. 5, 2010 (JP) ................ 2010-049813

(51) Int. Cl.
- A61B 1/04 (2006.01)
- A61B 1/00 (2006.01)
- A61B 5/07 (2006.01)
- A61B 5/05 (2006.01)
- G01B 7/14 (2006.01)
- H01H 9/00 (2006.01)

(52) U.S. Cl. ... 600/118; 600/117; 600/302; 324/207.13; 335/207

(58) Field of Classification Search ............. 600/118, 600/12, 117, 109, 160, 101, 424, 301, 407; 348/65; 324/207.13, 307, 309; 702/64; 340/686.1; 335/205–208

See application file for complete search history.

(56) References Cited

U.S. PATENT DOCUMENTS

| | | | |
|---|---|---|---|
| 7,295,226 B1 * | 11/2007 | Meron et al. | 348/77 |
| 7,766,167 B2 * | 8/2010 | Segawa | 206/439 |
| 7,770,725 B2 * | 8/2010 | Segawa | 206/363 |

(Continued)

FOREIGN PATENT DOCUMENTS

| | | |
|---|---|---|
| JP | 2005-095433 A | 4/2005 |
| JP | 2006-094933 A | 4/2006 |

(Continued)

OTHER PUBLICATIONS

International Search Report PCT/JP2011/051270 dated Mar. 1, 2011 together with partial English language translation.

(Continued)

*Primary Examiner* — John P Leubecker
*Assistant Examiner* — Ronald D Colque
(74) *Attorney, Agent, or Firm* — Scully Scott Murphy & Presser, PC

(57) ABSTRACT

A capsule endoscope that includes a capsule-shaped casing and a detecting unit that is provided inside the casing to detect a magnetic field orthogonal to a longitudinal direction of the casing, the endoscope being activated when the detecting unit detects a magnetic field of a threshold or more; a capsule container that houses the endoscope; a route portion in which a route is formed on which the container moves on a planar face; an activation magnetic field generating unit that is arranged at an interval along the route, and includes magnets for generating magnetic fields in a direction vertical to a direction in which the container moves on the route, the magnets being arranged such that respective magnetization directions are different; and a response unit that has a magnetization direction orthogonal respectively to a center axis direction of the longitudinal direction and a direction of the detected magnetic field.

13 Claims, 17 Drawing Sheets

U.S. PATENT DOCUMENTS

| | | | |
|---|---|---|---|
| 7,931,149 B2* | 4/2011 | Gilad et al. | 206/530 |
| 7,946,983 B2* | 5/2011 | Fujimori et al. | 600/302 |
| 2004/0254455 A1* | 12/2004 | Iddan | 600/424 |
| 2005/0272973 A1* | 12/2005 | Kawano et al. | 600/102 |
| 2007/0171012 A1* | 7/2007 | Fujimori et al. | 335/151 |
| 2007/0171013 A1* | 7/2007 | Fujimori et al. | 335/151 |
| 2007/0191671 A1* | 8/2007 | Kawano et al. | 600/12 |
| 2007/0221233 A1* | 9/2007 | Kawano et al. | 128/899 |
| 2007/0238988 A1* | 10/2007 | Minai | 600/424 |
| 2007/0265496 A1* | 11/2007 | Kawano et al. | 600/109 |
| 2008/0027267 A1* | 1/2008 | Segawa | 600/7 |
| 2008/0033243 A1* | 2/2008 | Meron et al. | 600/109 |
| 2008/0039675 A1* | 2/2008 | Segawa | 600/7 |
| 2008/0103372 A1* | 5/2008 | Segawa | 600/109 |
| 2008/0306358 A1* | 12/2008 | Minai | 600/302 |
| 2009/0093690 A1* | 4/2009 | Yoshizawa | 600/300 |
| 2009/0192353 A1* | 7/2009 | Segawa | 600/118 |
| 2009/0264702 A1* | 10/2009 | Yoshizawa | 600/117 |
| 2009/0275801 A1* | 11/2009 | Sakai | 600/117 |
| 2009/0292167 A1* | 11/2009 | Kimoto | 600/109 |
| 2009/0318762 A1* | 12/2009 | Segawa et al. | 600/118 |
| 2009/0326323 A1* | 12/2009 | Uchiyama et al. | 600/118 |
| 2010/0049033 A1* | 2/2010 | Kawano et al. | 600/424 |
| 2010/0121150 A1* | 5/2010 | Fujimori et al. | 600/118 |

FOREIGN PATENT DOCUMENTS

| | | |
|---|---|---|
| JP | 2006-223473 A | 8/2006 |
| WO | WO 2007/069698 A1 | 6/2007 |
| WO | WO 2007/083708 A1 | 7/2007 |

OTHER PUBLICATIONS

European Search Report dated Jul. 4, 2012 from corresponding European Patent Application No. EP 11 75 0419.1.

* cited by examiner

CAPSULE ENDOSCOPE ACTIVATION SYSTEM

CROSS-REFERENCE TO RELATED APPLICATIONS

This application is a continuation of PCT international application Ser. No. PCT/JP2011/051270 filed on Jan. 25, 2011 which designates the United States, incorporated herein by reference, and which claims the benefit of priority from Japanese Patent Application No. 2010-049813, filed on Mar. 5, 2010, incorporated herein by reference.

BACKGROUND OF THE INVENTION

1. Field of the Invention

The present invention relates to a capsule endoscope activation system which applies a magnetic field to a reed switch disposed inside a capsule endoscope to switch a driving state of the capsule endoscope from an off state to an on state.

2. Description of the Related Art

In recent years, swallowable type capsule endoscopes have been proposed in the field of an endoscope. This capsule endoscope is provided with an imaging function and a wireless communication function. The capsule endoscope has a function of, after the capsule endoscope is swallowed from a mouth of a subject (human body) for observation (examination), moving inside the body cavity such as the interior of an organ such as the stomach or small intestine according to peristaltic motions and sequentially capturing images until the capsule endoscope is spontaneously excreted.

Image data captured inside the body by the capsule endoscope while the capsule endoscope moves in the body cavity is sequentially transmitted to the outside by radio transmission and accumulated in memory provided outside. If the subject carries a receiving device which has a wireless communication function and a memory function, after swallowing the capsule endoscope, the subject can go where the subject likes until the endoscope is excreted. After the capsule endoscope is excreted, a doctor or nurse can make diagnosis by displaying images of organs on a display based on image data accumulated in the memory.

With this capsule endoscope, a reed switch which functions in response to a magnetic field applied from an outside is used to supply power from a power source to each function executing unit. Generally, with an existing reed switch, two magnetic reeds are arranged at a predetermined interval facing each other, and attract and contact each other when the magnetic field is applied in an axial direction of the reeds from an outside so as to electrically conduct between circuits. Further, by contrast with this, when the magnetic field is applied in the axial direction of the reeds from the outside, the reeds are separated, thereby releasing between circuits, and can electrically conduct between the circuits when the magnetic field is not applied. Hence, to switch between on and off of a power source using this reed switch, it is necessary to match a magnetic field direction and an axial direction of the reeds of the reed switch.

To realize the capsule endoscope having the above switch, for example, Japanese Laid-open Patent Publication No. 2005-95433 proposes a configuration where a capsule endoscope which has inside a reed switch which is turned on and off in response to an external magnetic field to control driving of the capsule endoscope is housed in a capsule container including a permanent magnetic which produces this external magnetic field. That is, the reed switch provided in the capsule endoscope adopts a structure which maintains the off state under environment in which the magnetic field of a certain intensity or more is applied, and is turned on when the intensity of the external magnetic field goes below a predetermined intensity. Therefore, in a state where the capsule endoscope is housed in the capsule container, the capsule endoscope is not driven. Further, by taking this capsule endoscope out of the capsule container upon swallowing, the capsule endoscope is spaced apart from the permanent magnet and is no longer influenced by the magnetism, and starts being driven.

SUMMARY OF THE INVENTION

A capsule endoscope activation system according to an aspect of the present invention includes a capsule endoscope that includes a capsule-shaped casing, and a magnetic field detecting unit that is provided inside the capsule-shaped casing and detects a magnetic field in a direction orthogonal to a longitudinal direction of the capsule-shaped casing, the capsule endoscope being activated when the magnetic field detecting unit detects a magnetic field of a threshold or more; a capsule container that houses the capsule endoscope; a route portion in which a route is formed on which the capsule container moves on a planar face; an activation magnetic field generating unit that is arranged at a predetermined interval along the route, and includes a plurality of magnets for generating magnetic fields in a direction vertical to a direction in which the capsule container moves on the route, the plurality of magnets being arranged such that respective magnetization directions are different; and a magnetic field response unit that has a magnetization direction orthogonal respectively to a center axis direction of the longitudinal direction and a direction of the magnetic field detected by the magnetic field detecting unit.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, preferred embodiments for implementing the present invention will be described in detail with reference to the drawings. In addition, the present invention is by no means limited to the following embodiments. Further, in the following description, each drawing only schematically illustrates the shape, size and positional relationship to an extent that content of the present invention can be understood. That is, the present invention is by no means limited only to the shape, size and positional relationship illustrated in each drawing.

First Embodiment

Figure 1:
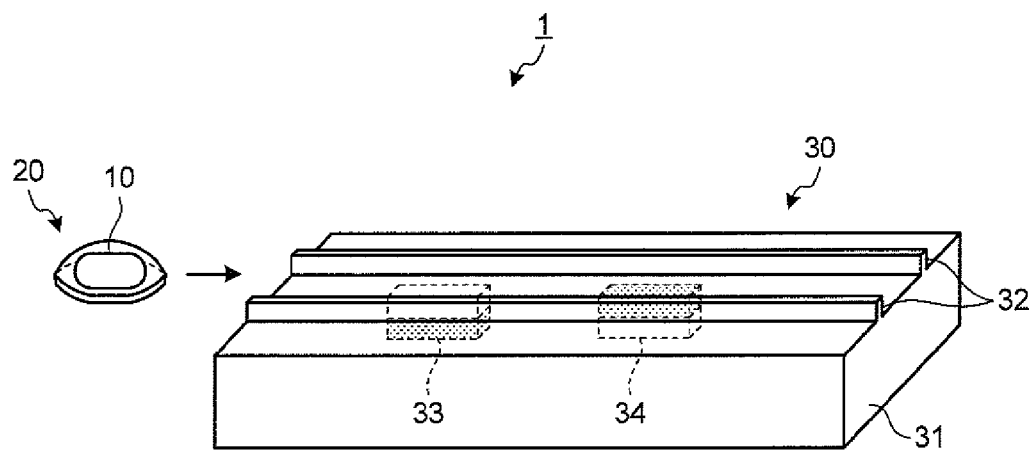
FIG. 1 is a perspective view schematically illustrating a capsule endoscope activation system according to a first embodiment of the present invention.

FIG. 1 is a perspective view schematically illustrating a capsule endoscope activation system 1 according to a first embodiment of the present invention. The capsule endoscope activation system 1 illustrated in FIG. 1 includes a capsule endoscope 10 which captures images (in-vivo intraluminal images) inside the subject, a capsule container 20 which houses the capsule endoscope 10 and an activation device 30 on which the capsule container 20 can slide and in which magnets are arranged such that magnetization directions are oriented toward predetermined directions. The activation device 30 has a setting face on which the capsule container 20 is set and can slide, and an activation magnetic field generating unit which includes a first activation magnetic field generating unit 33 and a second activation magnetic field generating unit 34 composed of permanent magnets which generate magnetic fields with respect to this setting face.

Figure 2:
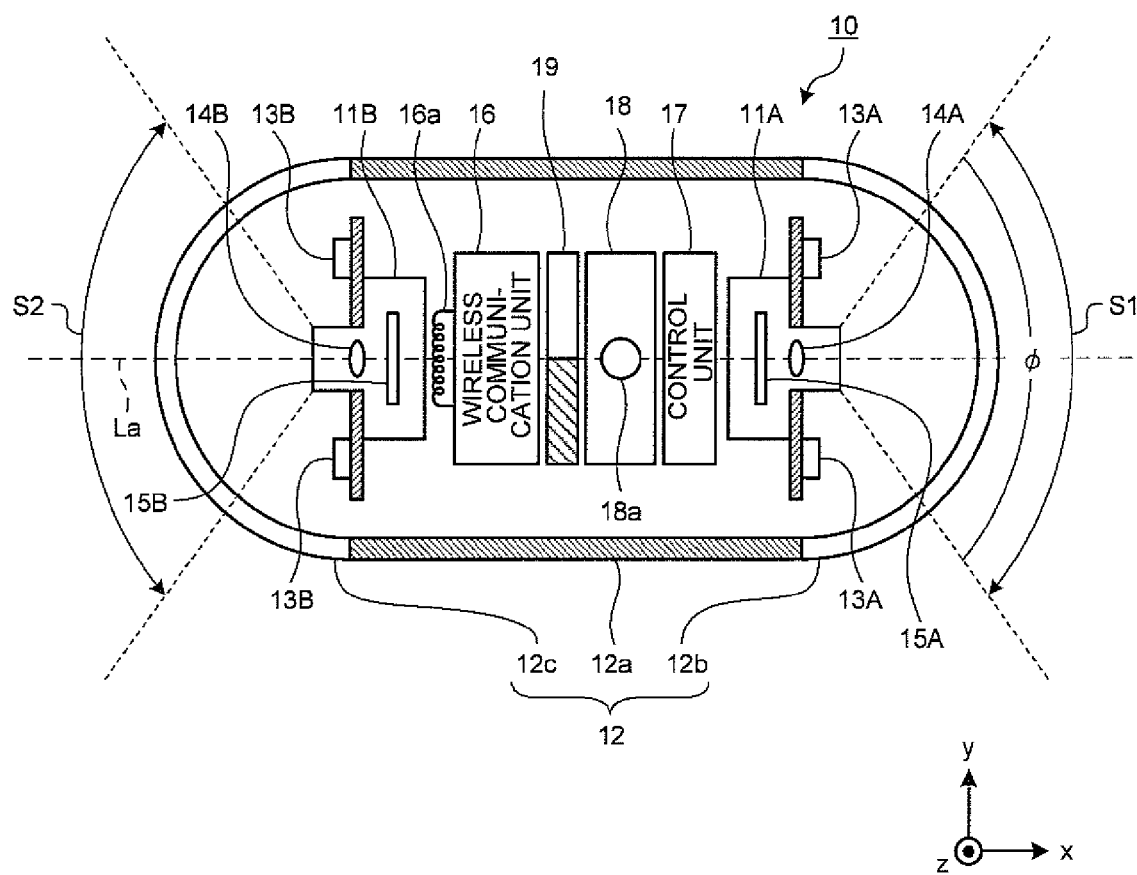
FIG. 2 is a sectional schematic view illustrating one configuration example of a capsule endoscope illustrated in FIG. 1.

The capsule endoscope 10 is a capsule medical device which is introduced inside an organ of the subject by way of, for example, oral injection to acquire in-vivo images of the subject, and has a built-in imaging function and wireless communication function. FIG. 2 is a sectional schematic view illustrating one configuration example of the capsule endoscope 10 illustrated in FIG. 1. As illustrated in FIG. 2, the capsule endoscope 10 has a capsule-shaped casing 12 which is an exterior shaped in a size which is easily introduced inside the organ of the subject, and imaging units 11A and 11B which capture images of the subject in different imaging directions. Further, the capsule endoscope 10 includes a wireless communication unit 16 which transmits by radio to the outside each image captured by the imaging units 11A and 11B, a control unit 17 which controls each component of the capsule endoscope 10 and a power source unit 18 which supplies power to each component of the capsule endoscope 10. Further, the capsule endoscope 10 includes a permanent magnet 19 which is a magnetic field response unit which can respond to an external magnetic field.

The capsule-shaped casing 12 is an outer casing formed in a size which can be introduced inside the organ of the subject, and is realized by blocking both of end openings of a cylindrical casing 12a by means of dome-shaped casings 12b and 12c. The dome-shaped casings 12b and 12c are dome-shaped optical members which are transparent with respect to light such as visible light at a predetermined wavelength band. The cylindrical casing 12a is a colored casing which is nearly opaque with respect to visible light. As illustrated in FIG. 2, the capsule-shaped casing 12 which is formed with these cylindrical casing 12a and dome-shaped casings 12b and 12c includes the imaging units 11A and 11B, the wireless communication unit 16, the control unit 17, the power source unit 18 and the permanent magnet 19 in a liquid-tight manner.

The imaging units 11A and 11B capture images in different imaging directions. More specifically, the imaging unit 11A includes illuminating units 13A such as LEDs, an optical system 14A such as a condenser lens and an imaging element 15A such as a CMOS image sensor or CCD. The illuminating unit 13A emits illumination light such as white light in an imaging field of view S1 of the imaging element 15A, and illuminates the subject (for example, the inner wall of the organ on the imaging field of view S1 side inside the subject) in the imaging field of view S1 beyond the dome-shaped casing 12b. The optical system 14A condenses reflected light from this imaging field of view S1, on an imaging face of the imaging element 15A, and forms a subject image in the imaging field of view S1, on the imaging face of the imaging element 15A. The imaging element 15A receives reflected light from this imaging field of view S1 through the imaging face, photoelectrically converts this received optical signal and captures subject images in this imaging field of view S1, that is, in-vivo images of the subject.

The imaging unit 11B includes illuminating units 13B such as LEDs, an optical system 14B such as a condenser lens and an imaging element 15B such as a CMOS image sensor or CCD. The illuminating unit 13B emits illumination light such as white light in an imaging field of view S2 of the imaging element 15B, and illuminates the subject (for example, the inner wall of the organ on the imaging field of view S2 side inside the subject) in the imaging field of view S2 beyond the dome-shaped casing 12c. The optical system 14B condenses reflected light from this imaging field of view S2, on an imaging face of the imaging element 15B, and forms a subject image in the imaging field of view S2, on the imaging face of the imaging element 15B. The imaging element 15B receives reflected light from this imaging field of view S2 through the imaging face, photoelectrically converts this received optical signal and captures subject images in this imaging field of view S2, that is, in-vivo images of the subject.

In addition, when the capsule endoscope 10 is a capsule medical device of a binocular type which captures images in the fore and rear of a long axis La direction as illustrated in FIG. 2, each optical axis of the imaging units 11A and 11B is nearly parallel to or nearly matches with the long axis La which is the center axis of the capsule-shaped casing 12 in the longitudinal direction. Further, each direction of the imaging fields of view S1 and S2 of the imaging units 11A and 11B, that is, each imaging direction of the imaging units 11A and 11B is the opposite direction.

The wireless communication unit 16 includes an antenna 16a, and sequentially transmits by radio to the outside each image captured by the above imaging units 11A and 11B through the antenna 16a. More specifically, the wireless communication unit 16 acquires from the control unit 17 an image signal of an in-vivo image of the subject captured by the imaging unit 11A or the imaging unit 11B, modulates this acquired signal and generates a radio signal obtained by modulating this image signal. The wireless communication unit 16 transmits the radio signal to an external transmitting/receiving unit (not illustrated) through the antenna 16a.

The control unit 17 controls each operation of the imaging units 11A and 11B and wireless communication unit 16 which are components of the capsule endoscope 10, and controls inputs and outputs of signals between these components. More specifically, the control unit 17 controls the imaging element 15A to capture images of the subject in the imaging field of view S1 illuminated by the illuminating unit 13A, and controls the imaging element 15B to capture images of the subject in the imaging field of view S2 illuminated by the illuminating unit 13B. Further, the control unit 17 has a signal processing function of generating image signals. Every time the control unit 17 acquires in-vivo image data (image data) in the imaging field of view S1 from the imaging element 15A, the control unit 17 performs predetermined signal processing of this image data and generates an image signal including image data of the imaging field of view S1. Similarly, every time the control unit 17 acquires image data in the imaging field of view S2 from the imaging element 15B, the control unit 17 performs predetermined signal processing of this image data and sequentially generates an image signal including image data of the imaging field of view S2. The control unit 17 controls the wireless communication unit 16 to sequentially transmit by radio to the outside each of a plurality of generated image signals in time sequences.

The power source unit 18 includes a battery unit such as a button-shaped battery or capacitor, and a magnetic field detecting unit 18a. The magnetic field detecting unit 18a is realized using a reed switch which is temporarily placed in a conduction state when detecting the magnetic field of a predetermined direction and a predetermined intensity (threshold) or more applied from the outside. The power source unit 18 switches the power source of the capsule endoscope 10 to an on state when the reed switch in placed in the conduction state, and adequately supplies power of the battery unit to each component of the capsule endoscope 10 (imaging units 11A and 11B, wireless communication unit 16 and control unit 17).

The permanent magnet 19 can magnetically respond to the magnetic field generated by the activation magnetic field generating unit. Further, the permanent magnet 19 can be used to magnetically guide the capsule endoscope 10 in the subject. The permanent magnet 19 is fixed and arranged inside the capsule-shaped casing 12.

Meanwhile, in the capsule endoscope 10, the long axis La, the magnetization direction of the permanent magnet 19 and the detection direction of the magnetic field detecting unit 18a are arranged orthogonally to each other to avoid a magnetic interference. For example, in FIG. 2, the long axis La is an x axis direction, the magnetization direction of the permanent magnet 19 is a y axis direction, and the detection direction of the magnetic field detecting unit 18a is a z axis direction.

Figure 3:
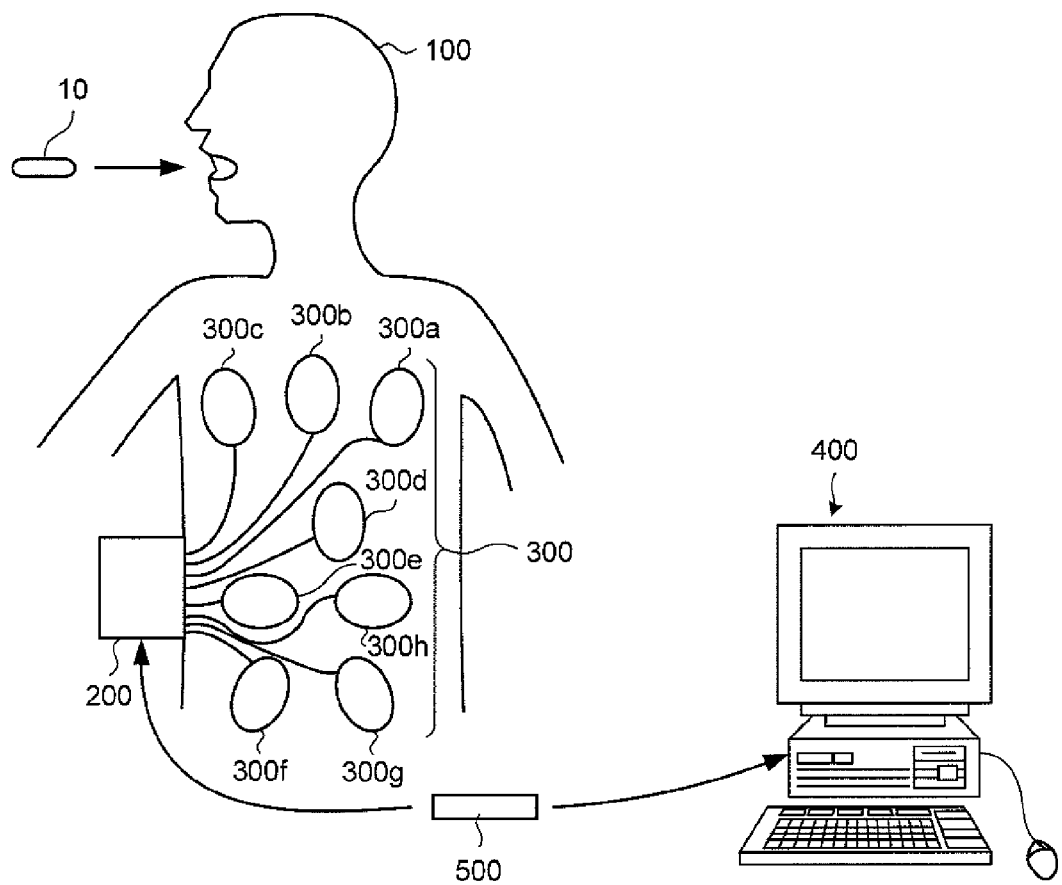
FIG. 3 is a schematic view illustrating an information acquiring system of the capsule endoscope according to the first embodiment of the present invention.

The capsule endoscope 10 is introduced inside the body of a subject 100 as illustrated in the schematic view of FIG. 3. The information acquiring system of the capsule endoscope illustrated in FIG. 3 transmits image data of a captured in-vivo image of the subject by radio to a receiving device 200, and includes the receiving device 200 which receives image data transmitted by radio from the capsule endoscope 10, an image display device 400 which displays the in-vivo image of the subject based on the image signal received by the receiving device 200 and a portable recording medium 500 which delivers, for example, image data between the receiving device 200 and the image display device 400.

The receiving device 200 includes a receiving antenna 300 including a plurality of antennas 300a to 300h attached to the surface outside the body of the subject 100. The receiving device 200 receives, for example, image data transmitted by radio from the capsule endoscope 10 through the receiving antenna 300, and associates each received image data with reception intensity information of each of the antennas 300a to 300h upon reception.

The antennas 300a to 300h are realized using, for example, loop antennas, and are arranged at predetermined positions on the surface outside the body of the subject 100, that is, positions associated with each organ inside the subject 100 in the passage route for the capsule endoscope 10. In addition, the antennas 300a to 300h may be disposed at predetermined positions on, for example, a jacket the subject 100 wears. In this case, the antennas 300a to 300h are disposed at predetermined positions on the surface outside the body of the subject 100 through, for example, this jacket. Further, arrangement of the antennas 300a to 300h can be changed at random according to the purpose of observation or diagnosis of the subject 100. In addition, the number of antennas of the receiving antenna 300 needs not be restrictively interpreted as eight of the antennas 300a to 300h, and may be less or more than eight.

The image display device 400 is realized by a work station which includes, for example, a CRT or liquid crystal display, and displays an image based on image data acquired through, for example, the portable recording medium 500. Further, the image display device 400 can also output image data to an output device such as a printer so as to display image data. In addition, the image display device 400 may have a function of communicating with an external device, and acquire or output image data by way of wired communication or wireless communication.

The portable recording medium 500 is realized by, for example, compact flash (registered trademark) memory, CD or DVD. The portable recording medium 500 is removable from the receiving device 200 and the image display device 400, and can output or record various pieces of information such as image data when the portable recording medium 500 is inserted to the receiving device 200 or the image display device 400. The portable recording medium 500 inserted to the receiving device 200 records, for example, image data received by the receiving device 200 from the capsule endoscope 10 while, for example, the capsule endoscope 10 is introduced inside the subject 100. Further, the capsule endoscope 10 is excreted from the subject 100, is then removed from the receiving device 200 and is inserted to the image display device 400, and outputs, for example, recorded image data to the image display device 400. The portable recording medium 500 delivers image data between the receiving device 200 and the image display device 400 in this way, so that the subject 100 can go where the subject 100 likes even while the capsule endoscope 10 is introduced. In addition, data may be delivered between the receiving device 200 and image display device 400 by way of wired communication or wireless communication.

Figure 4:
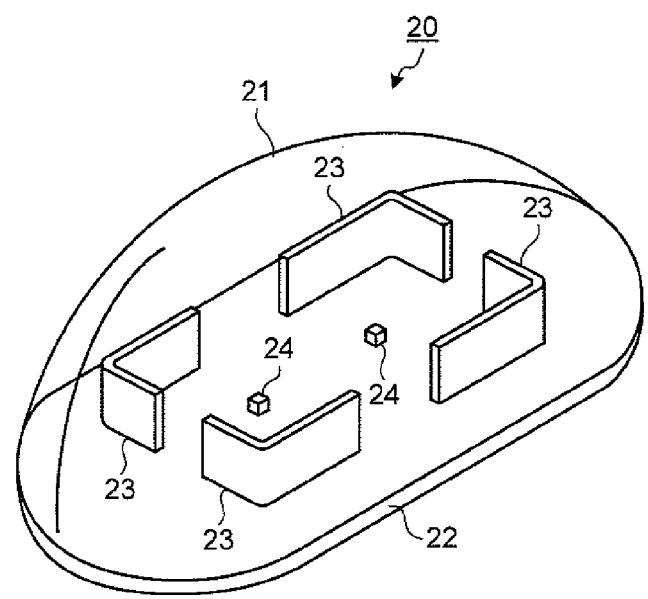
FIG. 4 is a perspective view illustrating a capsule container according to the first embodiment of the present invention.
Figure 5:
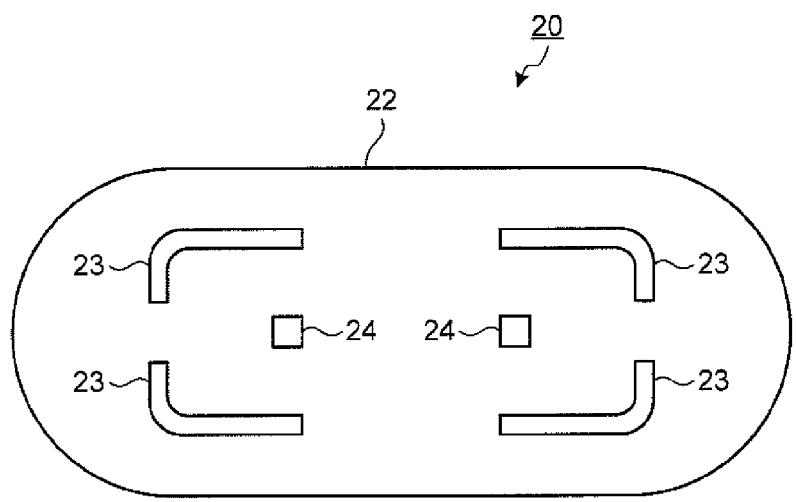
FIG. 5 is a plan view of the capsule container illustrated in FIG. 4 seen from above.
Figure 6:
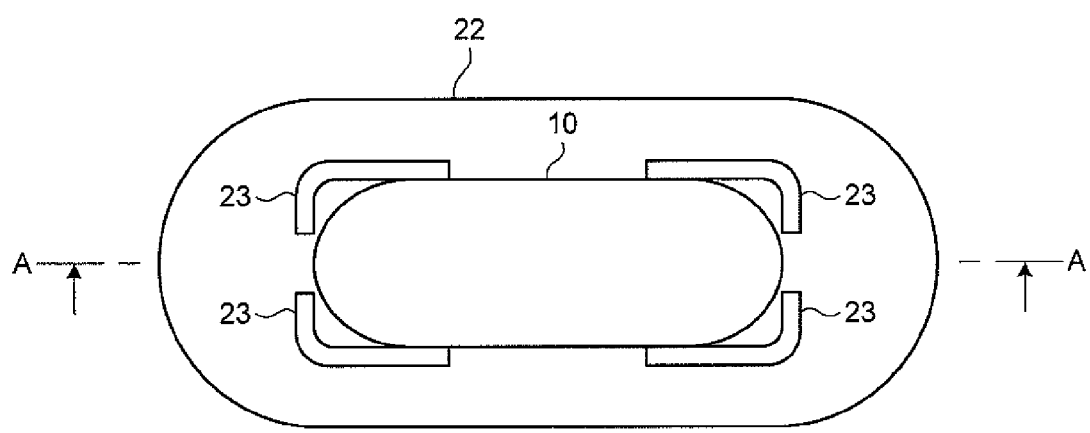
FIG. 6 is a plan view illustrating that the capsule endoscope is housed in the capsule container illustrated in FIG. 5.
Figure 7:
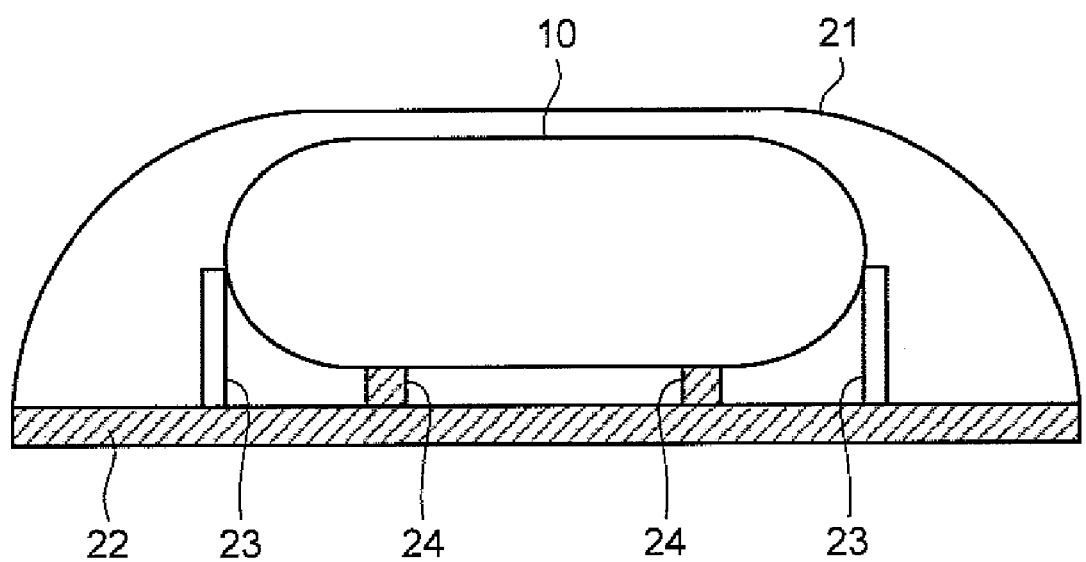
FIG. 7 is a partial sectional view of the capsule container illustrated in FIG. 6 in a cross section of A-A line.

Subsequently, the capsule container 20 will be described with reference to FIGS. 4 to 7. FIG. 4 is a perspective view illustrating the capsule container 20 according to the first embodiment of the present invention. FIG. 5 is a plan view of the capsule container 20 illustrated in FIG. 4 seen from above. FIG. 6 is a plan view illustrating that the capsule endoscope 10 is housed in the capsule container 20 illustrated in FIG. 5. Further, FIG. 7 is a partial sectional view where A-A line in FIG. 6 is the cross section.

The capsule container 20 has a flat bottom plate portion 22 which is slidable on the upper face of the activation device 30, and a cover 21 of a nearly bowl shape which has an opening of a nearly same shape as the outer periphery of the bottom plate portion 22 and covers the bottom plate portion 22.

The cover 21 is detachable to the bottom plate portion 22 and forms an enclosed space which can house the capsule endoscope 10 when the cover 21 is attached to the bottom plate portion 22. The cover 21 is transparent or semi-transparent, and is realized using a material which has permeability with respect to sterilization gas such as EOG (ethylene oxide gas). Consequently, it is possible to sterilize the capsule endoscope 10 to be housed inside. In addition, the degree of transparency of the cover 21 only needs to allow illumination light of the illuminating unit 13A and/or illuminating unit 13B of the capsule endoscope 10 to be visually checked through the cover 21.

The bottom plate portion 22 extends vertically with respect to the face which forms an internal space together with the cover 21, and has first support portions 23 which support a lateral face of the capsule endoscope 10 and second support portions 24 which support the bottom portion side of the capsule endoscope 10. As illustrated in FIG. 6, the first support portions 23 are formed to fit along the lateral face parallel to the long axis La of the capsule endoscope 10 when the capsule endoscope 10 is housed in the case. As illustrated in FIG. 7, the second support portions 24 have columnar shapes which support the lateral face of the bottom portion side of the capsule endoscope 10 in the long axis direction. The capsule endoscope 10 is supported rotatably by the first support portions 23 and the second support portions 24 by means of the long axis of the capsule endoscope 10 as a rotation axis.

Further, as illustrated in FIG. 1, the activation device 30 has a body portion 31 which has on the upper face a setting face on which the capsule container 20 is set and slides, guides 32 which project from the setting face at an interval equal to the width of the capsule container 20 (the length in a direction vertical to the long axis) and extends in the sliding direction of the capsule container 20, and the first activation magnetic field generating unit 33 and second activation magnetic field generating unit 34 which are arranged inside the body portion 31 and generate magnetic fields in predetermined directions.

The two guides 32 extend in parallel to each other, and are arranged such that the interval between the guides 32 is nearly equal to the width of the capsule container 20 in the lateral direction. The capsule endoscope 10 slides on a route formed between the guides 32 having this width to guide the capsule container 20 in the moving direction.

The first activation magnetic field generating unit 33 is realized using the permanent magnet 19, and is arranged inside the body portion 31 to be positioned below the setting face between the guides 32. The magnetization direction of the first activation magnetic field generating unit 33 is orthogonal to the setting face of the body portion 31. In addition, the first activation magnetic field generating unit 33 illustrated in FIG. 1 has an outlined S pole and a shaded N pole. Hence, the magnetization direction of the first activation magnetic field generating unit 33 is downward in FIG. 1.

Similar to the first activation magnetic field generating unit 33, the second activation magnetic field generating unit 34 is realized using the permanent magnet 19, and is arranged inside the body portion 31 to be positioned below the route between the guides 32. Further, the magnetization direction of the second activation magnetic field generating unit 34 is orthogonal to the setting face of the body portion 31. In addition, the second activation magnetic field generating unit 34 has an outlined S pole and a shaded N pole. Hence, the magnetization direction of the second activation magnetic field generating unit 34 is upward in FIG. 1.

The first activation magnetic field generating unit 33 and second activation magnetic field generating unit 34 are aligned at a predetermined interval in the body portion 31 along the route formed between the guides 32 below the setting face, and, when the capsule container 20 slides and is positioned nearby these activation magnetic field generating units, the capsule endoscope 10 housed in the capsule container 20 receives magnetic actions.

Next, activation of the capsule endoscope 10 by the capsule endoscope activation system 1 will be described with reference to FIG. 8 (FIGS. 8A to 8D) and FIG. 9. FIG. 8 is a view for describing rotation and activation of the capsule endoscope 10. FIG. 9 is a graph illustrating a relationship between a position of the capsule endoscope 10 and a magnetic field intensity applied in a direction (the direction of the y axis or z axis in FIG. 2) vertical to the long axis La of the capsule endoscope 10.

Figure 8A:
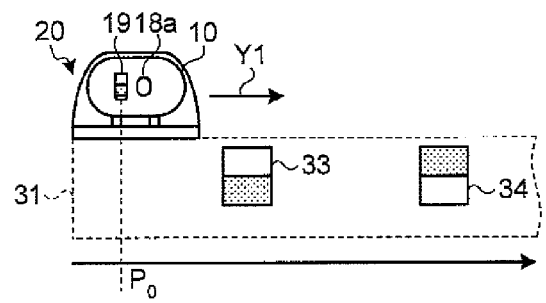
FIG. 8A is a view for describing rotation and activation of the capsule endoscope.
Figure 8B:
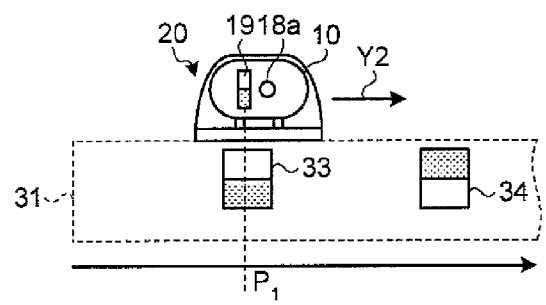
FIG. 8B is a view for describing rotation and activation of the capsule endoscope.
Figure 9:
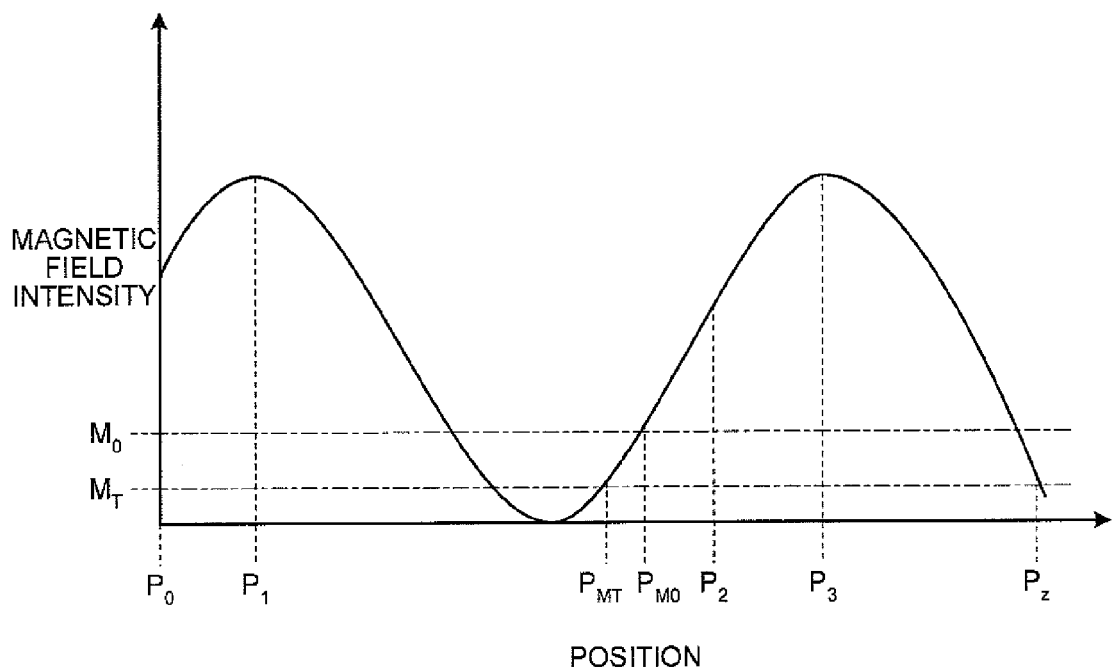
FIG. 9 is a graph illustrating a relationship between a position of the capsule endoscope and an absolute value of a magnetic field intensity applied in a direction vertical to a long axis of the capsule endoscope.

First, as illustrated in FIG. 8A, the capsule container 20 which houses the capsule endoscope 10 moves on the setting face of the body portion 31 in the direction indicated by an arrow Y1 in FIG. 8A, and comes close to the first activation magnetic field generating unit 33. When the position of the permanent magnet 19 in the horizontal direction in FIG. 8A is $P_0$, the magnetic field intensity read from the graph illustrated in FIG. 9 is applied to the capsule container 20 at this position $P_0$.

Then, when the capsule container 20 moves and the permanent magnet 19 reaches the center axis (position $P_1$) in the magnetization direction of the first activation magnetic field generating unit 33 (FIG. 8B), the permanent magnet 19 of the capsule endoscope 10 receives the maximum magnetic action from the first activation magnetic field generating unit 33 in the direction vertical to the long axis La. In response to this action, the permanent magnet 19 rotates such that the magnetization direction is oriented toward the same direction as the magnetization direction of the first activation magnetic field generating unit 33. In conjunction with this rotation, the capsule endoscope 10 rotates and the magnetic field detecting unit 18a also rotates. In addition, although the permanent magnet 19 does not stop rotating at the position $P_1$ depending on the speed at which the capsule container 20 slides, the permanent magnet 19 rotates such that at least the magnetization direction of the permanent magnet 19 is oriented toward the magnetization direction of the first activation magnetic field generating unit 33 at the point of time when the permanent magnet 19 passes $P_1$.

Figure 8C:
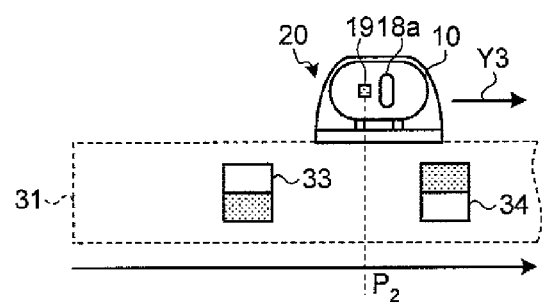
FIG. 8C is a view for describing rotation and activation of the capsule endoscope.
Figure 8D:
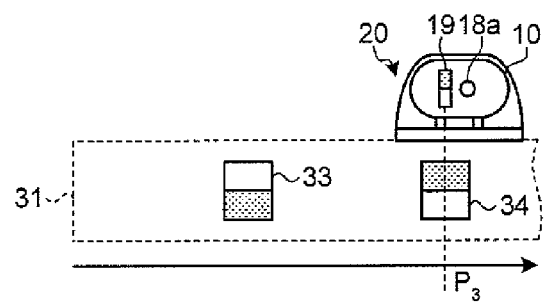
FIG. 8D is a view for describing rotation and activation of the capsule endoscope.

Meanwhile, as illustrated in FIG. 9, when the magnetic field intensity applied to the permanent magnet 19 exceeds $M_0$, the permanent magnet 19 rotates toward the direction in which the force is applied. That is, the capsule endoscope 10 starts rotating after the permanent magnet 19 passes the rotation start position $P_{M0}$ at which the magnetic field intensity $M_0$ is applied to the permanent magnet 19. When the capsule container 20 further moves in the direction of an arrow Y2, the permanent magnet 19 oriented in a predetermined magnetic field direction by the first activation magnetic field generating unit 33 comes close to the second activation magnetic field generating unit 34 which has an opposite magnetization direction from the first activation magnetic field generating unit 33. When the capsule endoscope 10 reaches the position $P_2$ near the intermediate point between the rotation start position $P_{M0}$ and center axis (position $P_3$) of the magnetization direction of the second activation magnetic field generating unit 34, the capsule endoscope 10 rotates to the position at which the magnetization direction of the permanent magnet 19 is vertical to the magnetization direction of the second activation magnetic field generating unit 34 (FIG. 8C).

Then, when the capsule container 20 further moves in the direction of an arrow Y3 and reaches the position $P_3$ (FIG. 8D), the permanent magnet 19 of the capsule endoscope 10 receives the maximum magnetic action in the direction vertical to the long axis La from the second activation magnetic field generating unit 34. In response to this action, the permanent magnet 19 rotates such that the magnetization direction is oriented toward the same direction as the magnetization direction of the second activation magnetic field generating unit 34. In conjunction with this rotation, the capsule endoscope 10 rotates and the magnetic field detecting unit 18a also rotates.

Between the rotation start position $P_{M0}$ and position $P_3$, the capsule endoscope 10 in the capsule container 20 is rotated at least 180 degrees about the long axis La in conjunction with the permanent magnet 19 in response to the magnetic field of the second activation magnetic field generating unit 34. Further, rotation of the capsule endoscope 10 causes rotation of the magnetic field detecting unit 18a about the long axis La, and the detection direction in which the magnetic field is detected also rotates. In this case, during rotation of the magnetic field detecting unit 18a, the detection direction of the magnetic field of the magnetic field detecting unit 18a matches with the magnetization direction of the second activation magnetic field generating unit 34. When the detection direction and magnetization direction match and the magnetic field detecting unit 18a detects the magnetic field, the power source unit 18 switches the power source to the on state and adequately supply power to each component of the capsule endoscope 10.

The magnetic field detecting unit 18a can set a threshold of the magnetic field intensity to be detected. For example, in FIG. 9, the magnetic field detecting unit 18a can detect the magnetic field of a predetermined threshold after passing a detection start position $P_{MT}$ at which the magnetic field has the magnetic field intensity $M_T$ or more. Further, the relationship between the magnetic field intensities from the first and second activation magnetic field generating units can be set at random, and is preferably set based on, for example, the magnitude of the magnetism of each activation magnetic field generating unit, the distance between the activation magnetic field generating units or a sliding speed of the capsule container.

In addition, although the above magnetic field detecting unit 18a rotates 180 degrees between the rotation start speed $P_{M0}$ and $P_3$, the magnetic field detecting unit 18a is oriented by the first activation magnetic field generating unit 33 and, when the magnetic field detecting unit 18a rotates again from the rotation start position $P_{M0}$ and rotates at least 90 degrees, matches with the magnetization direction of the second activation magnetic field generating unit 34, so that it is possible to turn on the switch. Further, the position range of rotation only needs to be at least 90 degrees in the range between the rotation start position $P_{M0}$ and the detection limit position $P_Z$ which is a detection limit range of the magnetic field detecting unit 18a which is on the opposite side of the first activation magnetic field generating unit 33 and detects the magnetic field of the second activation magnetic field generating unit 34.

Figure 10:
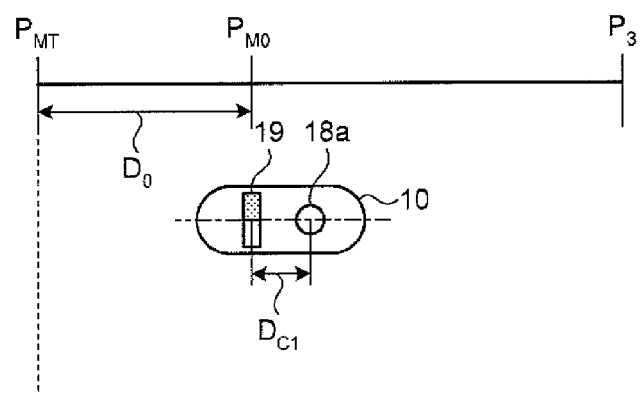
FIG. 10 is a schematic view illustrating a detection start position, a rotation start position and a detection limit position, and a distance relationship between a magnetic field detecting unit and a permanent magnet.

Next, the sliding speed of the capsule container 20 will be described with reference to FIG. 10. FIG. 10 is a schematic view illustrating the detection start position $P_{MT}$, rotation start position $P_{M0}$ and position $P_3$, and a distance relationship between the magnetic field detecting unit 18a and permanent magnet 19.

As illustrated in FIG. 10, the distance between the detection start position $P_{MT}$ and the rotation start position $P_{M0}$ is $D_0$, and the distance between the permanent magnet 19 and the magnetic field detecting unit 18a of the capsule endoscope 10 is $D_{C1}$. Meanwhile, the distance between the rotation start position $P_{M0}$ and the detection limit position $P_Z$ is $D_Z$, the time the magnetic field response unit 18a requires to rotate 180 degrees is $T_R$, the sliding speed of the capsule container 20 is $v_1$ and the distance the capsule container 20 travels to rotate 90 degrees is $D_{V1}$, the distance $D_{V1}$ is represented by the following Equation (1).

$$D_{V1} = v_1 \cdot T_R / 2 \qquad (1)$$

Further, when the magnetic field detecting unit 18a and permanent magnet 19 have the positional relationship illustrated in FIG. 10 and the magnetic field detecting unit 18a detects the magnetic field between the rotation start position $P_{M0}$ and detection limit position $P_Z$, the distance $D_{V1}$ needs to satisfy the following Equation (2).

$$D_{V1} \leq D_Z - D_{C1} \quad (2)$$

According to Equations (1) and (2), the following Equation (3) holds for the sliding speed $v_1$.

$$v_1 \leq 2(D_Z - D_{C1})/T_R \quad (3)$$

Consequently, by sliding the capsule container 20 according to the sliding speed $v_1$ satisfying Equation (3), the capsule endoscope 10 rotates at least 90 degrees between the rotation start position $P_{M0}$ and detection limit position $P_Z$, so that the detection direction of the magnetic field detecting unit 18a and magnetization direction of the second activation magnetic field generating unit 34 match and, consequently, the magnetic field detecting unit 18a can reliably detect the magnetic field.

Figure 11:
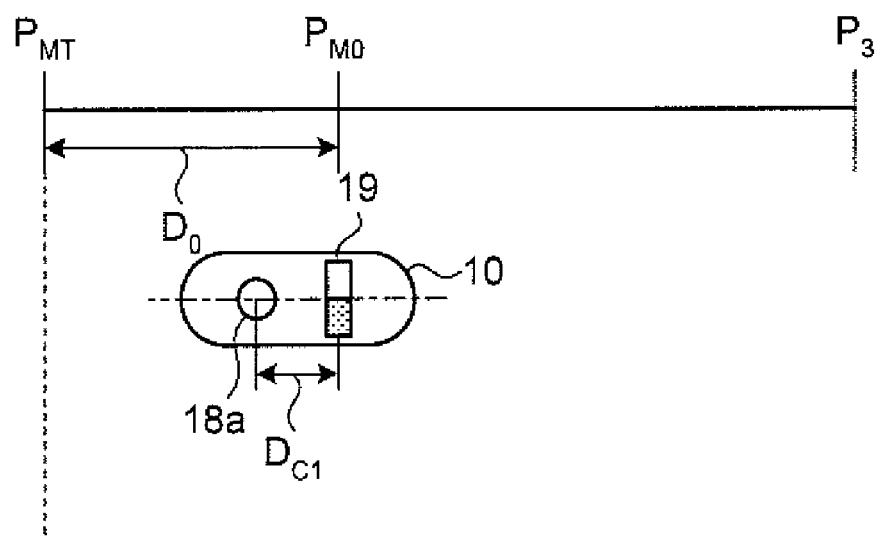
FIG. 11 is a schematic view illustrating another example of the distance relationship illustrated in FIG. 10.

Meanwhile, the sliding speed in case where the positional relationship between the magnetic field detecting unit 18a and permanent magnet 19 is reversed to the positional relationship illustrated in FIG. 10 will be described with reference to FIG. 11. FIG. 11 is a schematic view illustrating another example of the distance relationship illustrated in FIG. 10.

As illustrated in FIG. 11, the positions of the magnetic field detecting unit 18a and the permanent magnet 19 in the capsule endoscope 10 are reversed from FIG. 10 and arranged. This positional relationship is provided depending on the orientation of the capsule container 20 introduced in the sliding direction, and, when the permanent magnet 19 reaches the rotation start position $P_{M0}$, the magnet field response unit 18a is positioned behind the permanent magnet 19 in the sliding direction.

In this case, as illustrated in FIG. 11, when the distance $D_{C1}$ between the permanent magnet 19 and the magnetic field detecting unit 18a is shorter than the distance $D_0$ between the detection start position $P_{MT}$ and the rotation start position $P_{M0}$, if the capsule endoscope 10 rotates at least 90 degrees between the rotation start position $P_{M0}$ and the detection limit position $P_Z$, it is possible to detect the magnetic field. That is, when the capsule endoscope 10 rotates at least 90 degrees between the rotation start position $P_{M0}$ and the detection limit position $P_Z$, the magnetic field detecting unit 18a rotates at least 90 degrees between the detection start position $P_{MT}$ and the detection limit position $P_Z$, so that, in the detectable range, the detection direction and magnetization direction of the second activation magnetic field generating unit 34 match and, consequently, it is possible to place the power source in the on state.

Hence, when the distance $D_{C1}$ between the permanent magnet 19 and the magnetic field detecting unit 18a is shorter than the distance $D_0$ between the detection start position $P_{MT}$ and the rotation start position $P_{M0}$, the following Equation (4) holds for the sliding speed $v_2$ of the capsule container 20.

$$v_2 \leq 2D_Z/T_R \quad (4)$$

Even if the capsule endoscope activation system 1 according to the above first embodiment does not define the orientation about the long axis of the capsule endoscope 10 in a predetermined orientation when the capsule endoscope 10 is housed in the capsule container 20, the power source of the capsule endoscope 10 can be switched to the on state by rotating the capsule endoscope 10, so that it is possible to simplify the operation of housing the capsule endoscope 10 in the capsule container 20. Further, when the sliding speed is $v_1$ or $v_2$ according to each of the above conditions, it is possible to reliably place the power source in the on state.

Figure 12:
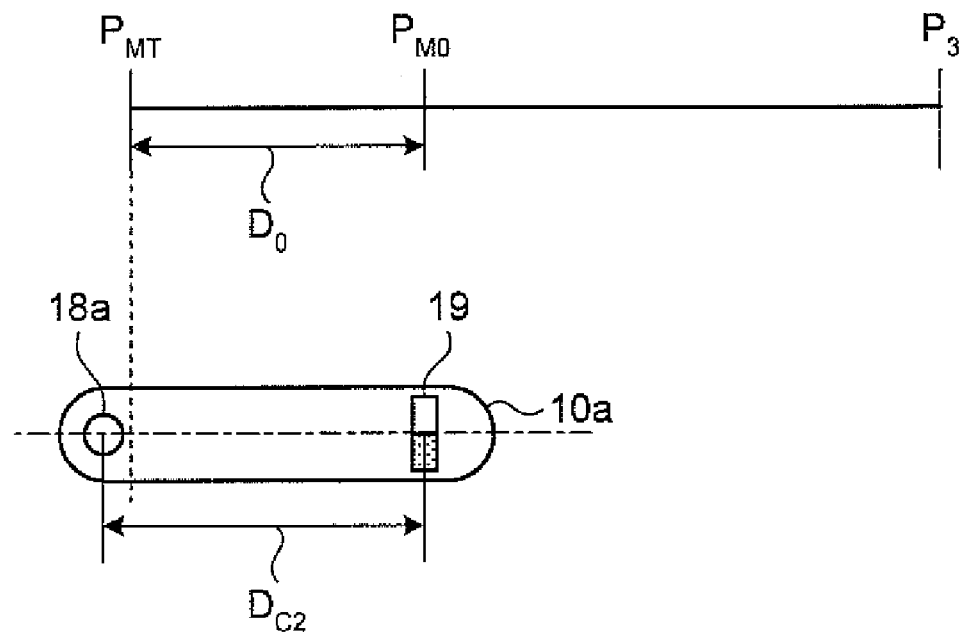
FIG. 12 is a schematic view illustrating another example of the distance relationship illustrated in FIG. 10.

In addition, although the distance $D_0$ between the detection start position $P_{MT}$ and the rotation start position $P_{M0}$ and the distance $D_{C1}$ between the permanent magnet 19 and the magnetic field detecting unit 18a of the capsule endoscope 10 have the relationship of $D_{C1} < D_0$, the reverse relationship may be provided. FIG. 12 is a schematic view illustrating another example of the distance relationship illustrated in FIG. 10. As illustrated in FIG. 12, when the distance $D_{C2}$ between the permanent magnet 19 and the magnetic field detecting unit 18a is longer than the distance $D_0$ between the detection start position $P_{MT}$ and the rotation start position $P_{M0}$, it is preferable that, before the magnetic field detecting unit 18a pass the detection start position $P_{MT}$, the capsule endoscope 10a do not rotate 90 degrees.

Hence, the difference between the distance $D_{C2}$ and the distance $D_0$ is set to the sliding speed $v_3$ at which the capsule endoscope 10 does not rotate 90 degrees. First, when the capsule endoscope 10 rotates 90 degrees, the distance is $D_{V3}$, the following Equation (5) holds.

$$D_{V3} > D_{C2} - D_0 \quad (5)$$

When $v_1$ of Equation (1) is substituted with $v_3$ in this Equation (5), the following Equation (6) satisfying the sliding speed $v_3$ to which the second modification is applicable is obtained.

$$v_3 > 2(D_{C2} - D_0)/T_R \quad (6)$$

By sliding the capsule endoscope 10 at the sliding speed $v_3$ satisfying Equation (6), the magnetic field detecting unit 18a can reliably detect the magnetic field, and it is possible to place the power source of the capsule endoscope 10 in the on state.

Figure 13:
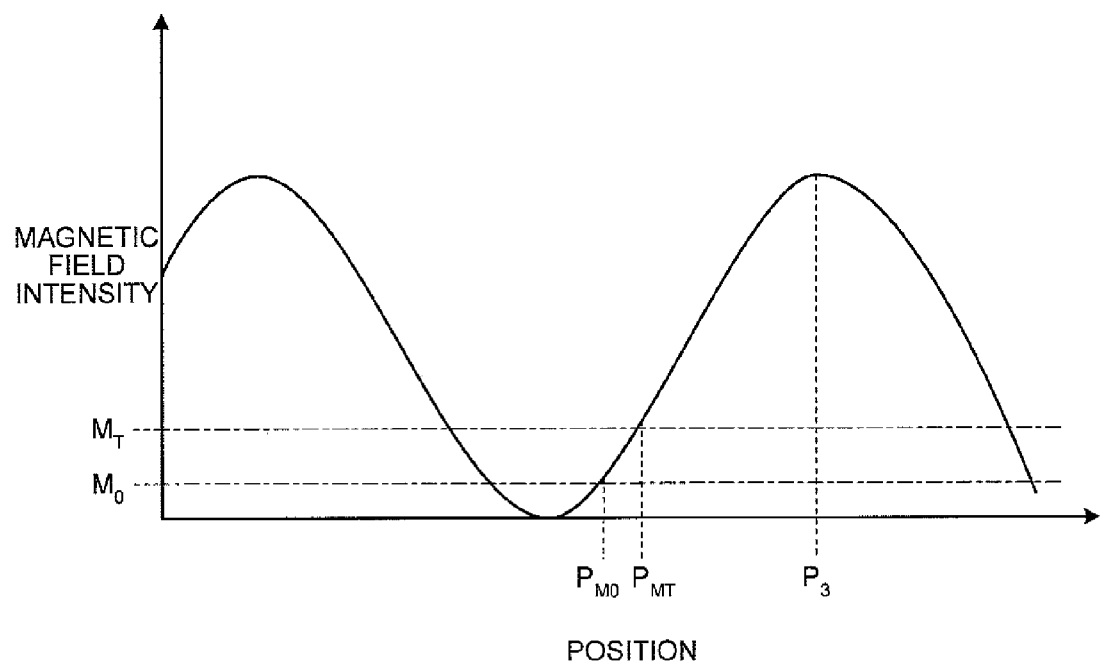
FIG. 13 is a graph illustrating a relationship between a position of the capsule endoscope and an absolute value of a magnetic field intensity applied in a direction vertical to a long axis of the capsule endoscope.
Figure 14:
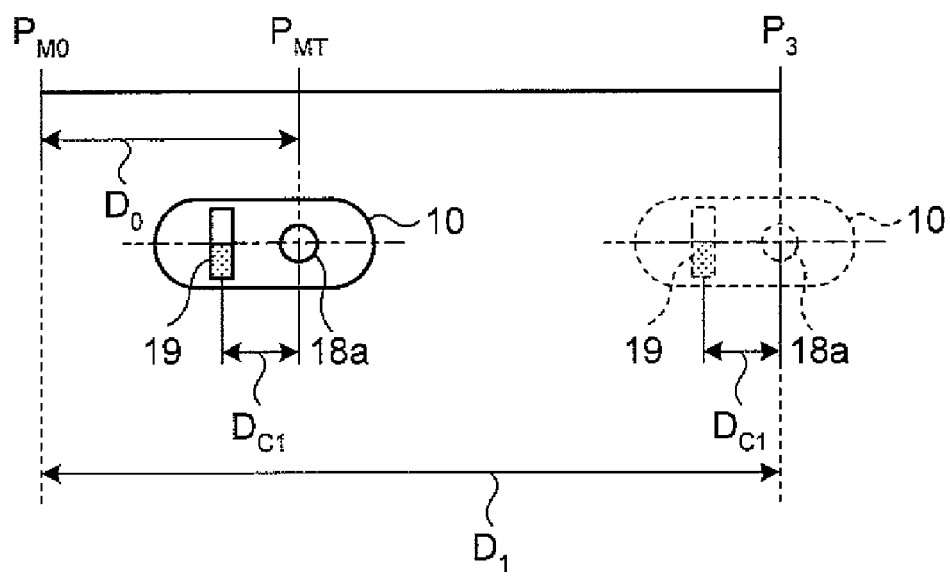
FIG. 14 is a schematic view illustrating another example of the distance relationship illustrated in FIG. 10.
Figure 15:
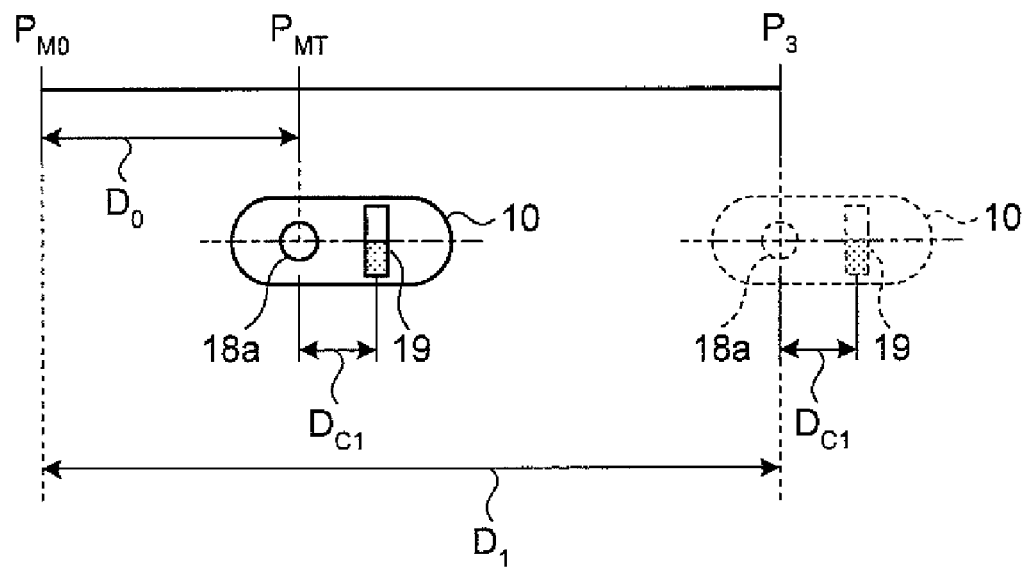
FIG. 15 is a schematic view illustrating another example of the distance relationship illustrated in FIG. 10.

Further, the relationship between the magnetic field intensity $M_0$ (rotation start position $P_{M0}$) at which the capsule endoscope 10 starts rotating and the magnetic field intensity $M_T$ (detection start position $P_{MT}$) which allows detection of the magnetic field may be reversed. A sliding speed in case where the magnetic field intensity relationship between the detection start position $P_{MT}$ and the rotation start position $P_{M0}$ is reversed from FIG. 9 will be described with reference to FIGS. 13 to 15. FIG. 13 is a graph illustrating a relationship between a position of the capsule endoscope and an absolute value of a magnetic field intensity applied in a direction vertical to a long axis of the capsule endoscope. FIGS. 14 and 15 are schematic views illustrating another example of the distance relationship illustrated in FIG. 10.

As illustrated in FIG. 13, according to the relationship of the magnetic field intensity, a significant magnetic field intensity $M_T$ at which the magnetic field detecting unit 18a can start detection is set with respect to the magnetic field intensity $M_0$ at which the capsule endoscope 10 can start rotation.

FIG. 14 illustrates that the positional relationship between the magnetic field detecting unit 18a and the permanent magnet 19 is the same as the positional relationship illustrated in FIG. 10. In this case, two conditions are preferably satisfied where the capsule endoscope 10 which has passed the rotation start position $P_{M0}$ does not rotate 90 degrees before the magnetic field detecting unit 18a passes the detection start position $P_{MT}$, and rotates 90 degrees or more before the second activation magnetic field generating unit 34 passes an arrangement position $P_3$.

With the above two conditions, when the capsule endoscope 10 rotates 90 degrees, the moving distance $D_{V4}$ and the distance between the rotation start position $P_{M0}$ and the arrangement position $P_3$ of the second activation magnetic field generating unit 34 is $D_1$, the following Equations (7) and (8) are obtained.

$$D_{V4} > D_0 - D_{C1} \quad (7)$$

$$D_{V4} \leq D_1 - D_{C1} \quad (8)$$

By substituting $v_1$ of Equation (1) with $v_4$ in Equations (7) and (8), the following Equation (9) is obtained.

$$2(D_0-D_{C1})/T_R < v_4 \leq 2(D_1-D_{C1})/T_R \quad (9)$$

By sliding the capsule endoscope 10 at the sliding speed $v_4$ satisfying Equation (9), the magnetic field detecting unit 18a can reliably detect the magnetic field, and it is possible to place the power source of the capsule endoscope 10 in the on state.

Further, FIG. 15 illustrates that the positional relationship between the magnetic field detecting unit 18a and the permanent magnet 19 is reversed from the positional relationship illustrated in FIG. 10. In this case, two conditions are preferably satisfied where the capsule endoscope 10 which has passed the rotation start position $P_{M0}$ does not rotate 90 degrees before the magnetic field detecting unit 18a passes the detection start position $P_{MT}$, and rotates 90 degrees or more before the second activation magnetic field generating unit 34 passes the arrangement position $P_3$.

With the above two conditions, when the capsule endoscope 10 rotates 90 degrees, the moving distance $D_{V5}$ and the distance between the rotation start position $P_{M0}$ and the arrangement position $P_3$ of the second activation magnetic field generating unit 34 is $D_1$, the following equations (10) and (11) are obtained.

$$D_{V5} > D_0 + D_{C1} \quad (10)$$

$$D_{V5} \leq D_1 + D_{C1} \quad (11)$$

From Equations (10) and (11), and Equation (1), the following Equation (12) is obtained.

$$2(D_0+D_{C1})/T_R < v_5 \leq 2(D_1+D_{C1})/T_R \quad (12)$$

By sliding the capsule endoscope 10 at the sliding speed $v_5$ satisfying Equation (12), the magnetic field detecting unit 18a can reliably detect the magnetic field, and it is possible to place the power source of the capsule endoscope 10 in the on state.

As described above, by sliding the capsule container 20 at one of the sliding speeds $v_1$ to $v_5$ satisfying each condition, and rotating the capsule endoscope 10 to match the detection direction of the magnetic field detecting unit 18a and the magnetization direction of the activation magnetic field generating unit, it is possible to reliably place the power source in the on state.

Figure 16:
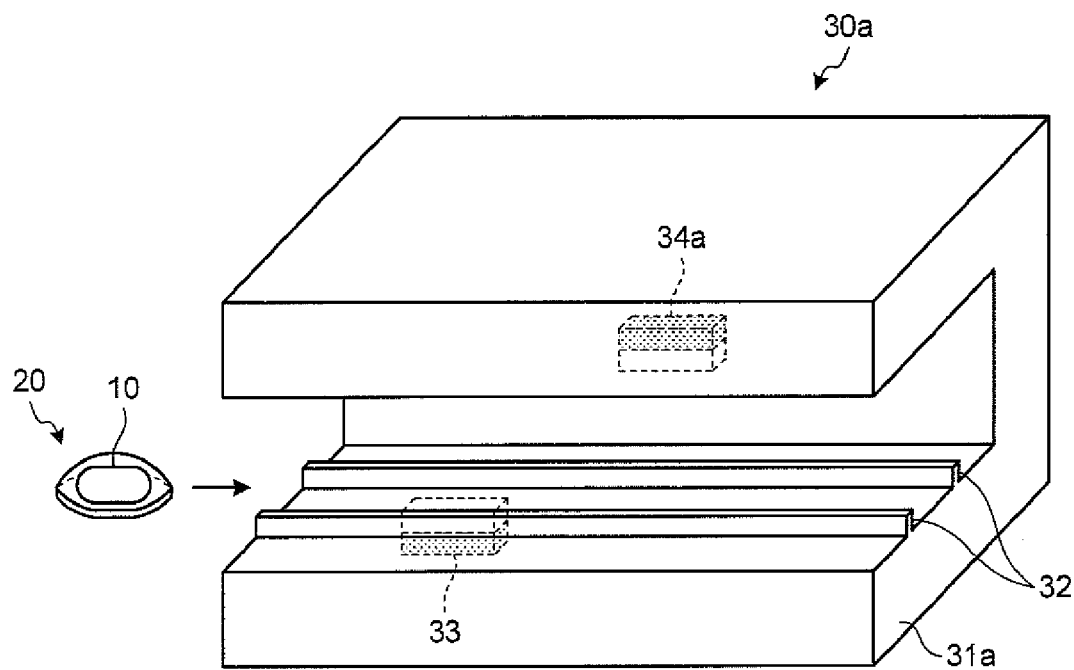
FIG. 16 is a perspective view schematically illustrating a capsule endoscope activation system according to a modification of the first embodiment.

Further, although the first embodiment has been described where the first activation magnetic field generating unit 33 and the second activation magnetic field generating unit 34 are arranged on a planar face including a route and on one side of this route, the first activation magnetic field generating unit 33 and the second activation magnetic field generating unit 34 may be arranged in upper and lower directions of the capsule container 20 which slides on the setting face. FIG. 16 is a perspective view schematically illustrating the capsule endoscope activation system according to a modification of the first embodiment.

The capsule endoscope activation system illustrated in FIG. 16 includes the first activation magnetic field generating unit 33 which is disposed on a lower side of the capsule container 20 which slides on the setting face of a body portion 31a of an activation device 30a, and a second activation magnetic field generating unit 34a which is disposed on the upper side. Further, the first activation magnetic field generating unit 33 and the second activation magnetic field generating unit 34a are arranged such that the magnetization directions are the opposite directions with respect to the sliding capsule container 20, for example, in FIG. 16, the magnetization direction of the first activation magnetic field generating unit 33 is the downward direction and the magnetization direction of the second activation magnetic field generating unit 34a is the upward direction.

With the above arrangement according to the modification, by sliding the capsule container 20, the capsule endoscope 10 housed in the capsule container 20 can be rotated about the long axis La, so that it is possible to reliably place the power source in the on state.

Second Embodiment

Figure 17:
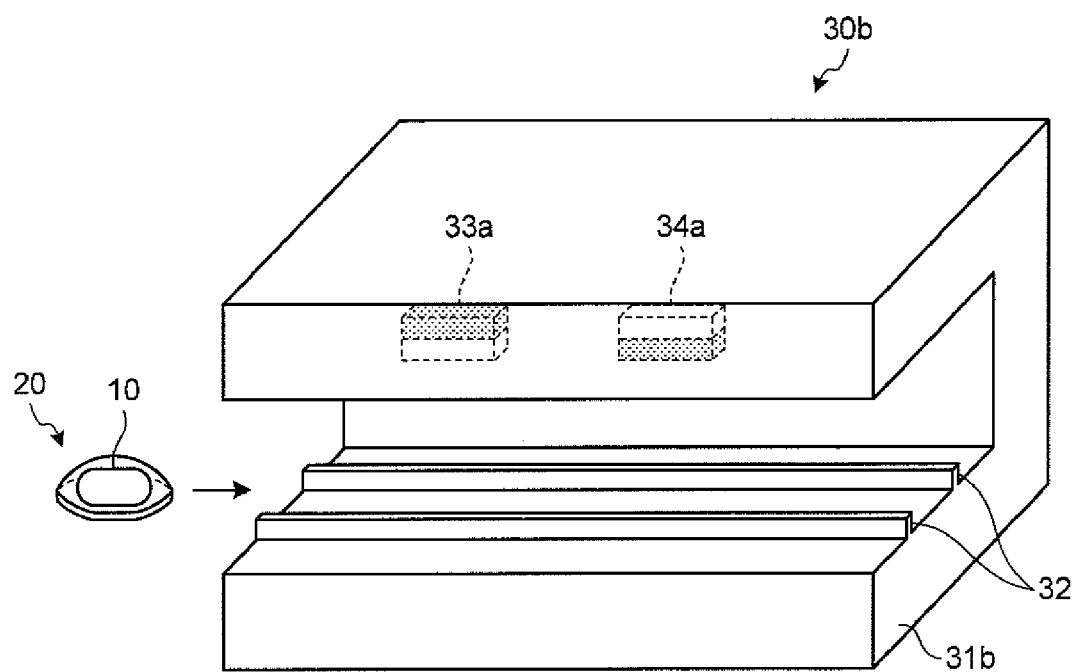
FIG. 17 is a perspective view schematically illustrating a capsule endoscope activation system according to a second embodiment of the present invention.

Next, a capsule endoscope activation system according to a second embodiment of the present invention will be described with reference to FIG. 17. FIG. 17 is a perspective view schematically illustrating a capsule endoscope activation system according to the second embodiment of the present invention. With the capsule endoscope activation system illustrated in FIG. 17, in a body portion 31b of an activation device 30b, a first activation magnetic field generating unit 33a and the second activation magnetic field generating unit 34a which are an activation magnetic field generating unit are disposed above a capsule container 20 which slides along the route formed between the guides 32 and on a setting face.

The first activation magnetic field generating unit 33a and the second activation magnetic field generating unit 34a are aligned and provided above the sliding/setting face of the body portion 31b, and disposed such that the magnetization directions pass the capsule container 20 on the setting face, more particularly, a capsule endoscope 10, and are opposite directions from each other. According to this configuration, it is possible to apply the magnetic field to the capsule endoscope 10 housed when the capsule container 20 passes, and rotate the capsule endoscope 10, and place the power source in the on state.

Particularly, with the capsule endoscope activation system according to the second embodiment, the activation magnetic field generating units are arranged above the capsule container 20, and, when a permanent magnet 19 of the capsule endoscope 10 rotates in response to the magnetic field from the activation magnetic field generating unit, if the vertical upward force is applied from the activation magnetic field generating unit, the force in the direction opposite to the gravity works, so that it is possible to reduce, for example, a frictional force applied upon rotation of the capsule endoscope 10, and more efficiently rotate the capsule endoscope 10.

Figure 18:
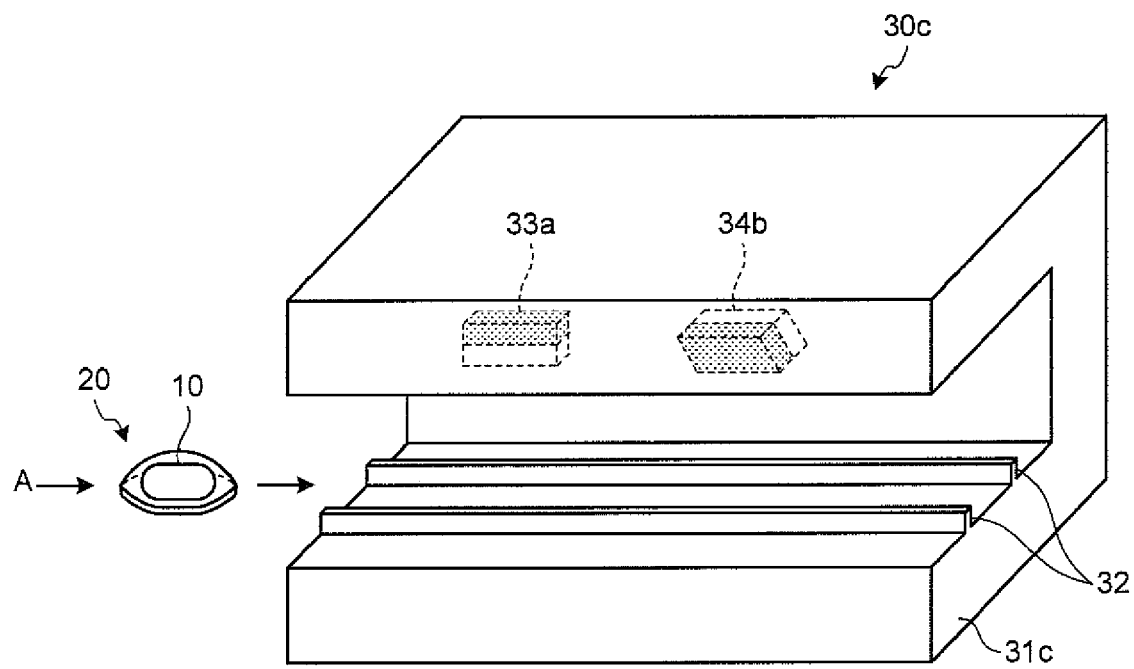
FIG. 18 is a perspective view schematically illustrating a capsule endoscope activation system according to a first modification of the second embodiment.
Figure 19:
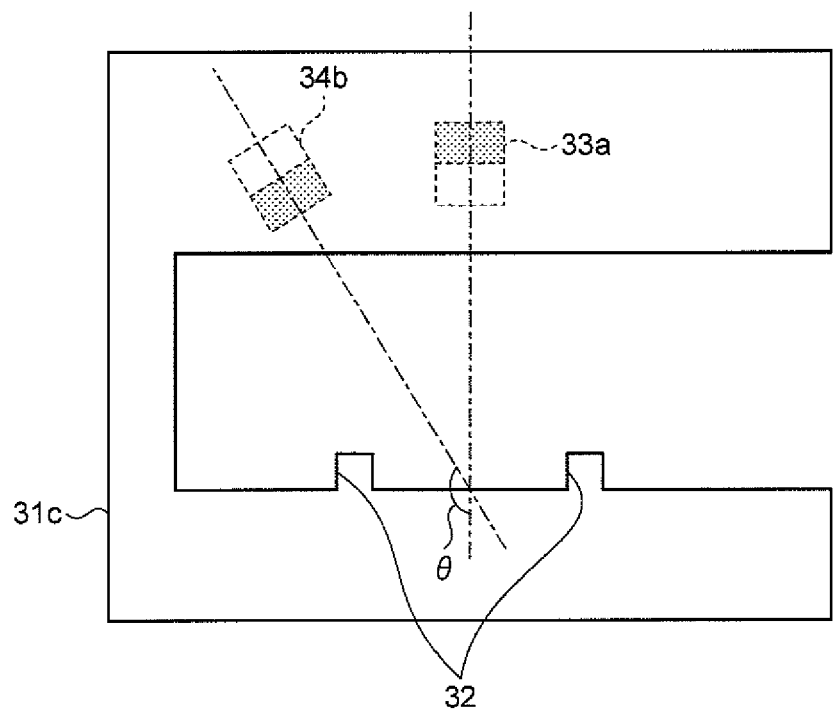
FIG. 19 is a plan view of the capsule endoscope activation system illustrated in FIG. 18 viewed in the direction of arrow A.

In addition, although the activation magnetic field generating units illustrated in FIG. 17 are aligned along the moving direction of the capsule container, the activation magnetic field generating units may be arranged by varying angles of the magnetization directions. FIG. 18 is a perspective view schematically illustrating a capsule endoscope activation system according to a first modification of the second embodiment. FIG. 19 is a plan view of the capsule endoscope activation system illustrated in FIG. 18 viewed in the direction of arrow A.

In a body portion 31c of an activation device 30c illustrated in FIGS. 18 and 19, one of the first activation magnetic field generating unit 33a and a second activation magnetic field generating unit 34b according to the first modification is disposed to incline toward the upper side of the setting face on which the capsule container 20 slides. The magnetization directions of the first activation magnetic field generating unit 33a and the second activation magnetic field generating unit 34b are disposed to pass the capsule container 20, more particularly, the capsule endoscope 10, and be different from each other. According to the first modification, as illustrated in FIG. 19, the second activation magnetic field generating unit 34b is arranged such that the magnetization direction (indicated by a broken line in FIG. 19) is inclined in the route formed between the guides 32.

Also with this first modification, the first activation magnetic field generating unit 33a and the second activation magnetic field generating unit 34b are arranged such that, while the angle formed between the magnetization directions is 90 degrees or less, force components in a direction vertical to the setting face are opposite, so that, when the capsule container 20 moves from the first activation magnetic field generating unit 33a to the second activation magnetic field generating unit 34b and the capsule endoscope 10 rotates at the angle θ as illustrated in FIG. 19, the capsule endoscope 10 rotates 90 degrees or more and, consequently, the magnetic field detecting unit 18a can detect the magnetic field and it is possible to place the power source of the capsule endoscope 10 in the on state.

Figure 20:
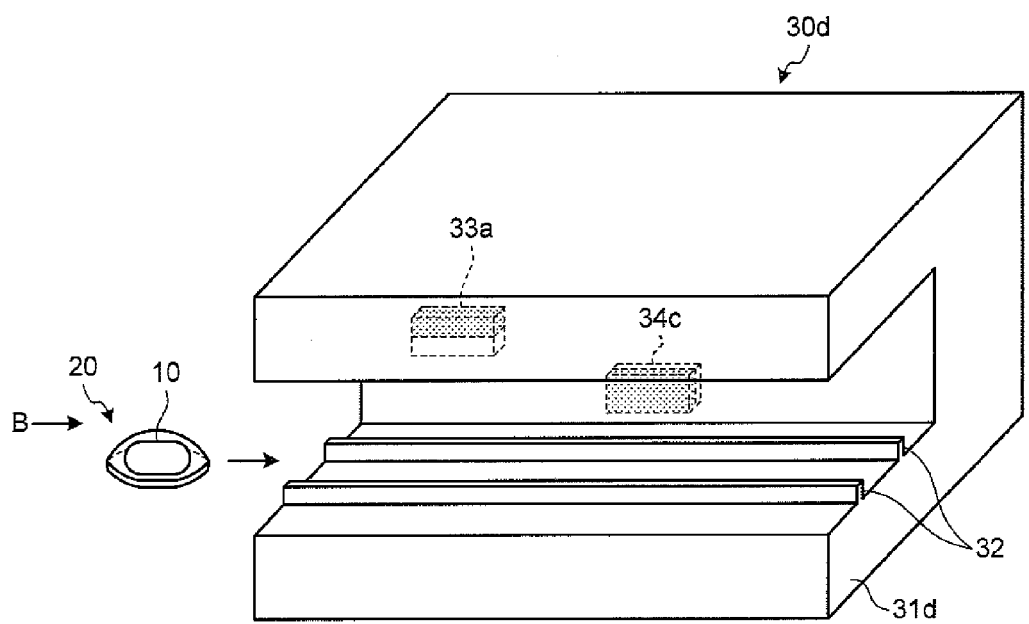
FIG. 20 is a perspective view schematically illustrating a capsule endoscope activation system according to a second modification of the second embodiment.
Figure 21:
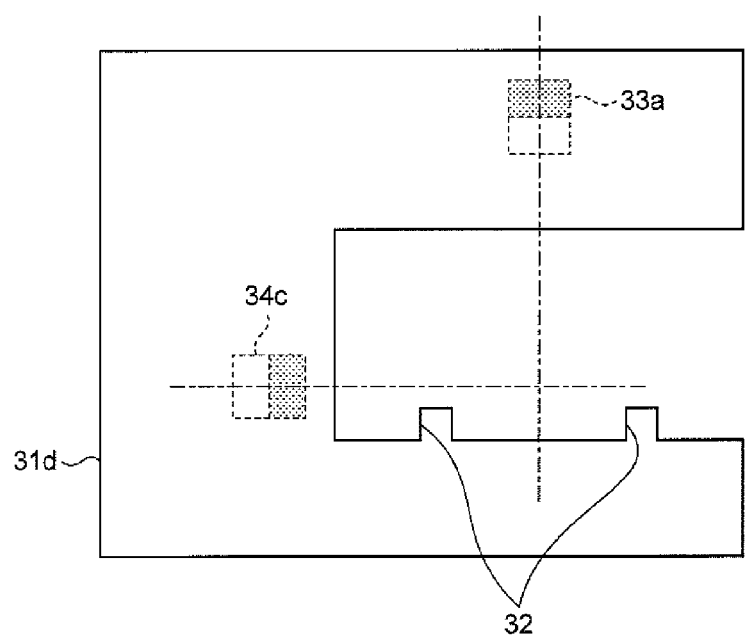
FIG. 21 is a plan view of the capsule endoscope activation system illustrated in FIG. 20 viewed in the direction of arrow B.

Further, FIG. 20 is a perspective view schematically illustrating a capsule endoscope activation system according to a second modification of the second embodiment. FIG. 21 is a plan view of the capsule endoscope activation system illustrated in FIG. 20 viewed in the direction of arrow B. In a body portion 31d of an activation device 30d illustrated in FIGS. 20 and 21, the first activation magnetic field generating unit 33a and a second activation magnetic field generating unit 34c according to the second modification are disposed on the upper side of the setting face on which the capsule container 20 slides, such that the magnetization directions pass the capsule endoscope 10 and are orthogonal to each other.

The first activation magnetic field generating unit 33a and second activation magnetic field generating unit 34c are disposed such that the magnetization directions are orthogonal. Meanwhile, the capsule endoscope 10 rotated by the first activation magnetic field generating unit 33a in a predetermined direction rotates 90 degrees or 270 degrees following subsequent sliding of the capsule container 20. In this case, when the capsule endoscope 10 rotates 270 degrees, the second activation magnetic field generating unit 34c, magnetization direction and detection direction match during rotation, so that it is possible to place the power source in the on state.

By contrast with this, when the capsule endoscope 10 rotates 90 degrees, while the capsule endoscope 10 rotates in response to the magnetic action received from the second activation magnetic field generating unit 34c, the detection direction of the magnetic field detecting unit 18a does not match with the magnetization direction of the second activation magnetic field generating unit 34c. In this case, when the capsule endoscope 10 rotates 90 degrees, the magnetic field detecting unit 18a detects the magnetic field of the first activation magnetic field generating unit 33a having the matching magnetization direction upon rotation, and the power source of the capsule endoscope 10 is placed in the on state. Hence, when the capsule endoscope 10 rotates 90 degrees, the interval between the first activation magnetic field generating unit 33a and the second activation magnetic field generating unit 34c is preferably adjusted such that, when the capsule endoscope 10 is rotated in a predetermined direction by the second activation magnetic field generating unit 34c, the magnetic field intensity of the first activation magnetic field generating unit 33a is a detection threshold of the magnetic field detecting unit 18a or more.

In addition, when the arrangement of the activation magnetic field generating units according to the second modification has the relationship between the detection start position $P_{MT}$ and the rotation start position $P_{MO}$ illustrated in FIG. 9, there are cases where, while the capsule container 20 slides between the detection start position $P_{MT}$ and the rotation start position $P_{MO}$, the power source of the capsule endoscope 10 is placed in the on state.

Figure 22:
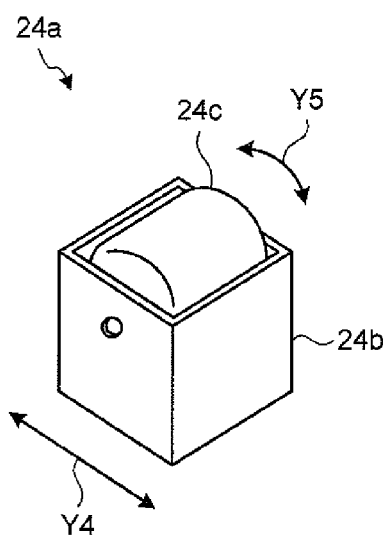
FIG. 22 is a perspective view schematically illustrating a modification of a second support portion of the capsule endoscope activation system according to the present invention.

With the second embodiment, the second support portions 24 of the capsule container 20 may be provided with rotation members which are rotatable in the rotation direction of the capsule endoscope 10. FIG. 22 is a perspective view schematically illustrating a modification of the second support portion 24 of the capsule endoscope activation system according to the present invention.

The second support portion 24a illustrated in FIG. 22 is provided on the upper face of the bottom plate portion 22 illustrated in FIG. 4, and has a casing 24b which has a space inside, and a rotation member 24c which is supported by the casing 24b axially in the longitudinal direction of this column and is rotatable.

The rotation member 24c is housed in the internal space to slightly project from the upper part of the casing 24b, and supports the capsule endoscope 10 on the upper face of this projecting portion. The rotation member 24c is supported by the casing 24b to rotate in a direction (Y5) parallel to the rotation direction Y4 of the capsule endoscope 10. That is, when the rotation member 24c supports the capsule endoscope 10, the rotation member 24c is rotatable about the axis parallel to the long axis La of the capsule endoscope 10. In addition, by covering the contact face of the rotation member 24c with respect to the capsule endoscope 10 using, for example, resin, the frictional force with respect to the capsule endoscope 10 may be increased. When the frictional force is increased, the rotation member 24c rotates in conjunction with the capsule endoscope 10, so that the frictional force in the rotation direction of the capsule endoscope 10 is reduced, and it is possible to more reliably realize rotation of the capsule endoscope 10. In addition, the present embodiment is also applicable to the first embodiment.

Third Embodiment

Figure 23:
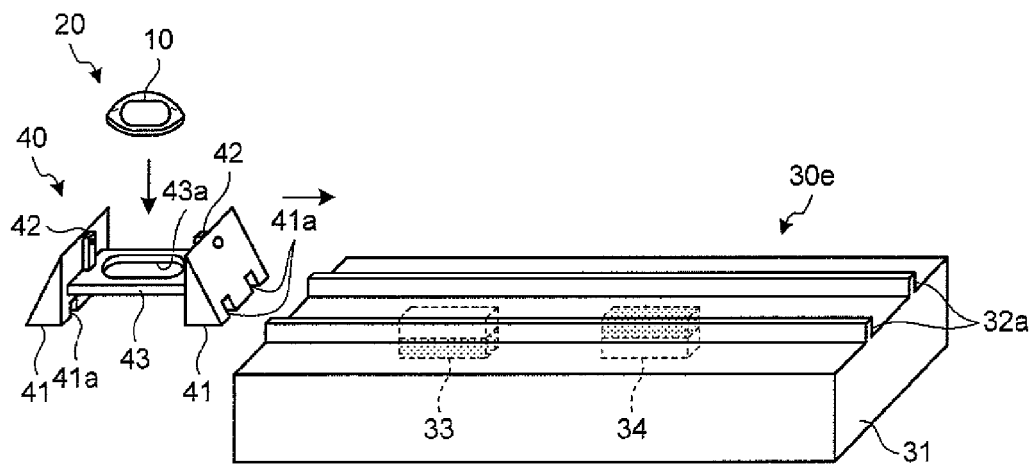
FIG. 23 is a perspective view schematically illustrating a capsule endoscope activation system according to a third embodiment of the present invention.
Figure 24:
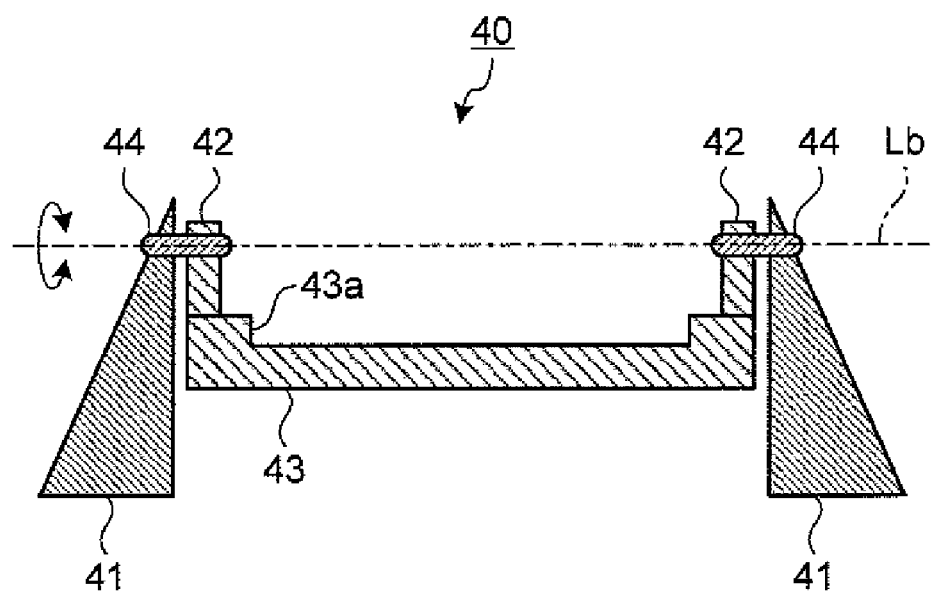
FIG. 24 is a sectional view of a planar face which passes the long axis of each support column of a rotating device illustrated in FIG. 23.
Figure 25:
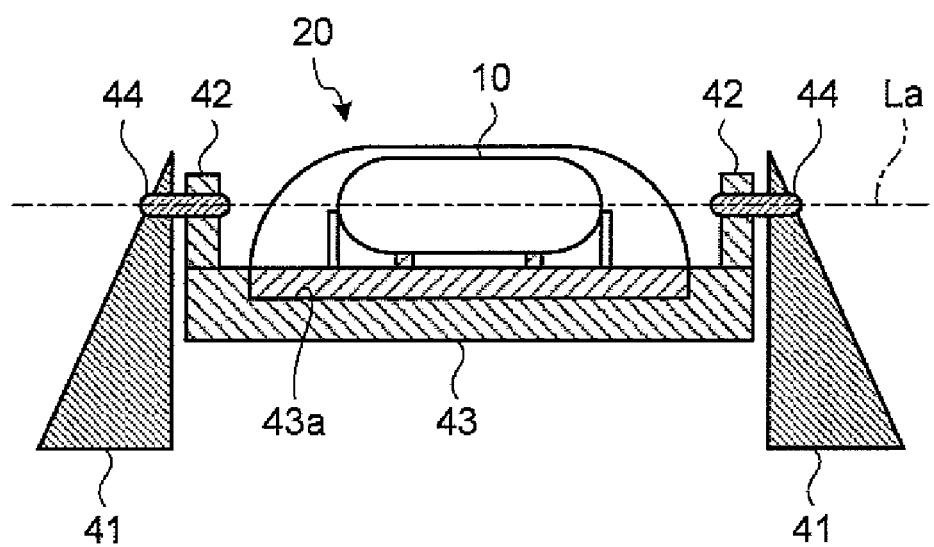
FIG. 25 is a partial sectional view illustrating a state where a capsule container which houses the capsule endoscope is set in the sectional view illustrated in FIG. 24.

Next, a capsule endoscope activation system according to a third embodiment of the present invention will be described with reference to FIG. 23. FIG. 23 is a perspective view schematically illustrating a capsule endoscope activation system according to the third embodiment of the present invention. Further, FIG. 24 is a sectional view of a planar face which passes the long axis of each support column 42 of a rotating device 40 illustrated in FIG. 23. FIG. 25 is a partial sectional view illustrating a state where a capsule container 20 which houses a capsule endoscope 10 is set in the sectional view illustrated in FIG. 24.

The capsule endoscope activation system illustrated in FIG. 23 has the capsule container 20 which houses the capsule endoscope 10, a rotating device 40 on which the capsule container 20 is rotatably set and which slides on an activation device 30e, and the activation device 30e on which a first activation magnetic field generating unit 33 and second activation magnetic field generating unit 34 which are activation magnetic field generating units and have predetermined magnetization directions are disposed.

The activation device 30e has a body portion 31 which has on the upper face a setting face on which the capsule container 20 can slide, guides 32a which project from the setting face at an interval nearly equal to the width (length in a direction vertical to the long axis) of the capsule container and extend in a direction in which the rotation device 40 needs to slide, and the first activation magnetic field generating unit 33 and second activation magnetic field generating unit 34 which are disposed inside the body portion 31 and between the guides 32a and have predetermined magnetization directions, respectively.

The guides 32a function as a route portion, are arranged at the width nearly equal to the capsule container 20 and form a route between the guides 32a to guide the sliding direction of the rotating device 40.

As illustrated in FIGS. 23 and 24, the rotating device 40 has a holding portion 43 which has a housing portion 43a which can fit with and hold the capsule container 20, columnar support columns 42 which extend in a direction vertical to a formation face of the housing portion 43a of the holding portion 43, and rotation support portions 41 which rotatably support the support columns 42 and the holding portion 43 through support members 44 which support the support columns 42. In addition, the housing portion 43a has a space which can hold the capsule container 20 to an extent that the capsule container 20 is not detached when the holding portion 43 rotates and is oriented reverse.

Further, when the capsule container 20 is set, as illustrated in FIG. 25, the support columns 42 and the holding portion 43 are rotatably supported by the support members 44 using a long axis La of the capsule endoscope 10 as a rotation axis. Meanwhile, in a state where the capsule container 20 is housed in the housing portion 43a, an axial line Lb of the support members 44 illustrated in FIG. 24 and the long axis La match. In addition, each support portion of the capsule container 20 fixes and supports the capsule endoscope 10 (not illustrated). For example, the surfaces of the support portions are covered by, for example, resin having a high frictional force. By this means, the capsule container 20 rotates in conjunction with rotation of the capsule endoscope 10, and therefore, by applying rotative power to the holding portion 43 following rotation of the capsule endoscope 10, the holding portion 43 is rotated about the support members 44. In this case, the capsule endoscope 10 rotates about the long axis La of the center axis.

As illustrated in FIG. 23, the above rotating device 40 has concave portions 41a meeting the guides 32a, in the bottom portion of each rotation support portion 41. When the rotation device 40 slides on the activation device 30e, the rotation device 40 is guided in the sliding direction by latching the concave portions 41a and the guides 32a, and slides in a predetermined direction.

With the capsule endoscope activation system according to the third embodiment employing the above configuration, the rotating device 40 is guided on the guides 32a and slides on the upper face of the body portion 31, and receives magnetic actions in predetermined directions from the first activation magnetic field generating unit 33 and the second activation magnetic field generating unit 34, the holding portion 43 rotate about the axial line Lb of the support members 44 in response to these actions in conjunction with rotation of the permanent magnet 19 of the capsule endoscope 10, so that the magnetic field detecting unit 18a of the capsule endoscope 10 can detect the magnetic field and, consequently, it is possible to place the power source of the capsule endoscope 10 in the on state.

Figure 26:
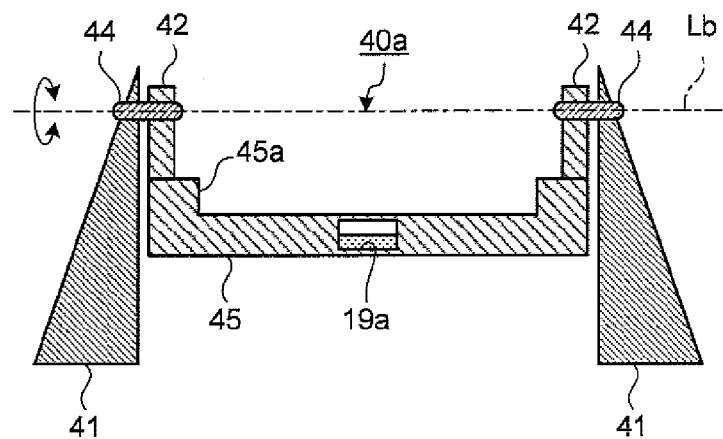
FIG. 26 is a partial sectional view illustrating a modification of a rotating device according to the third embodiment.

In addition, with the third embodiment, when the capsule endoscope 10 does not have the permanent magnet 19, a magnet only needs to be provided in a holding portion or capsule container. FIG. 26 is a partial sectional view illustrating a modification of a rotating device according to the third embodiment.

With a rotating device 40a illustrated in FIG. 26, a permanent magnet 19a is arranged inside a holding portion 45. The permanent magnet 19a is disposed such that the magnetization direction is vertical to the axial line direction of the support members 44. More preferably, when the capsule endoscope 10 is housed in a housing portion 45a through the capsule container 20, the permanent magnet 19a is arranged such that the magnetization direction is parallel to a planar face vertical to the long axis La of the capsule endoscope 10.

Meanwhile, depending on the orientation of the capsule endoscope 10 housed in the capsule container 20, there are cases where the power source of the capsule endoscope 10 is placed in the on state when the capsule container 20 is housed in the housing portion 45a.

When the above rotating device 40a slides on the activation device 30e illustrated in FIG. 23, the rotating device 40a receives magnetic actions from the first activation magnetic field generating unit 33 and second activation magnetic field generating unit 34 and the permanent magnet 19a rotates the holding portion 45 in response to these actions, so that it is possible to change the detection direction of the capsule container 20 housed in the housing portion 45a and the magnetic field detecting unit 18a of the capsule endoscope 10, and place the power source of the capsule endoscope 10 in the on state.

Fourth Embodiment

Figure 27:
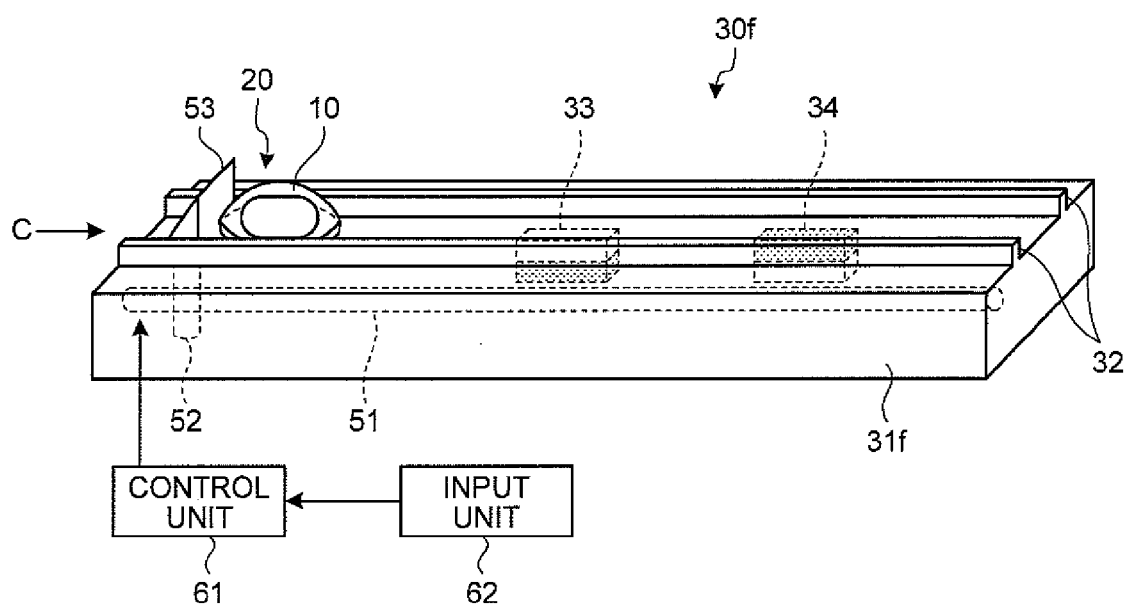
FIG. 27 is a perspective view schematically illustrating a capsule endoscope activation system according to a fourth embodiment of the present invention.
Figure 28:
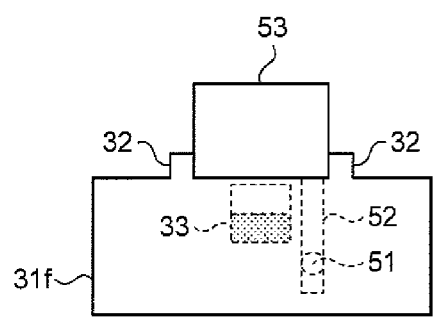
FIG. 28 is a plan view of the capsule endoscope activation system illustrated in FIG. 27 viewed in the direction of arrow C.

Although, with the first to third embodiments, the capsule container and rotating device are manually slid on the activation device, the capsule container and rotating device may be automatically slid by a control unit. FIG. 27 is a perspective view schematically illustrating a capsule endoscope activation system according to a fourth embodiment of the present invention. FIG. 28 is a plan view of the capsule endoscope activation system illustrated in FIG. 27 viewed in the direction of arrow C.

An activation device 30f according to the fourth embodiment has a rotation shaft 51 of a nearly columnar shape which extends in parallel to guides 32, a shaft penetration portion 52 which extends in a direction orthogonal to the rotation shaft 51, fits to and penetrates the rotation shaft 51 and is movable in a direction in which the rotation shaft 51 extend using rotative power of the rotation shaft 51, a moving member which is arranged on the upper face of a body portion 31f and in the route formed by the guides 32, has a width nearly equal to the width between the guides 32 and which has a moving auxiliary member 53 coupled to the shaft penetration portion 52, a control unit 61 which controls rotary driving of the rotation shaft 51 and an input unit 62 which inputs a command to the control unit 61 to rotate and drive the rotation shaft 51.

As illustrated in the plan view of FIG. 28, the rotation shaft 51 and the shaft penetration portion 52 are disposed without hitting an activation magnetic field generating unit (first activation magnetic field generating unit 33). Preferably, the shaft penetration portion 52 is disposed to be movable in the space between the activation magnetic field generating unit and the guides 32.

When receiving information of a command to rotate and drive the rotation shaft 51 from the input unit 62, the control unit 61 rotates and drives the rotation shaft 51 about the long axis of the rotation shaft 51. When the rotation shaft 51 rotates, the shaft penetration portion 52 moves in an extending direction of the rotation shaft 51. In conjunction with movement of the shaft penetration portion 52, the moving auxiliary member 53 moves along the guides 32.

When this moving auxiliary member 53 pushes a capsule container 20 arranged between the guides 32, a capsule endoscope 10 housed in the capsule container 20 can receive magnetic actions from activation magnetic field generating units, and, in response to the above actions, it is possible to place the power source of the capsule endoscope 10 in the on state.

In addition, with the fourth embodiment, the control unit 61 preferably controls the moving speed of the shaft penetration portion 52 according to sliding speeds $v_1$ to $v_5$ matching the above respective conditions.

Fifth Embodiment

Figure 29:
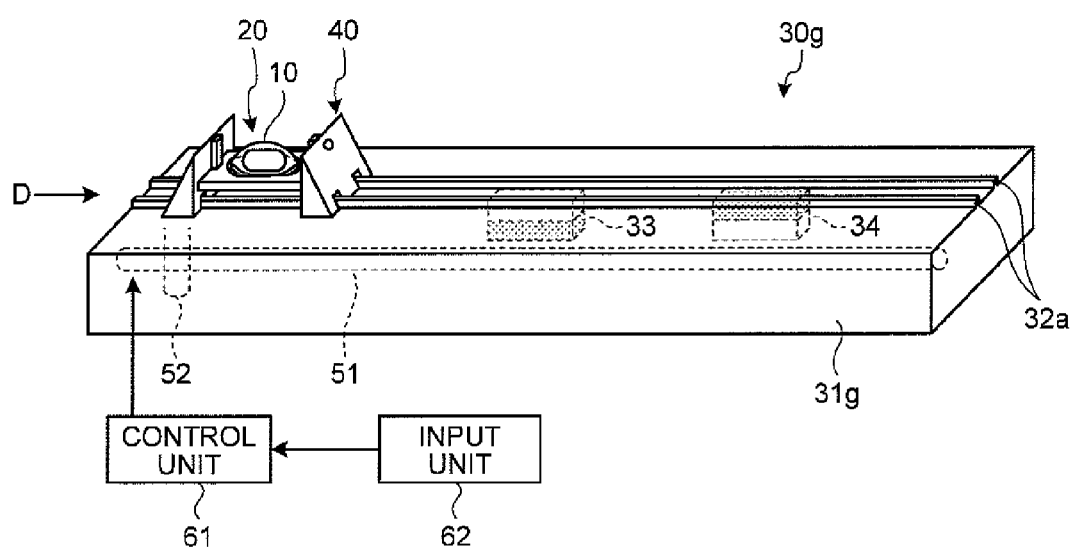
FIG. 29 is a perspective view schematically illustrating a capsule endoscope activation system according to a fifth embodiment of the present invention.
Figure 30:
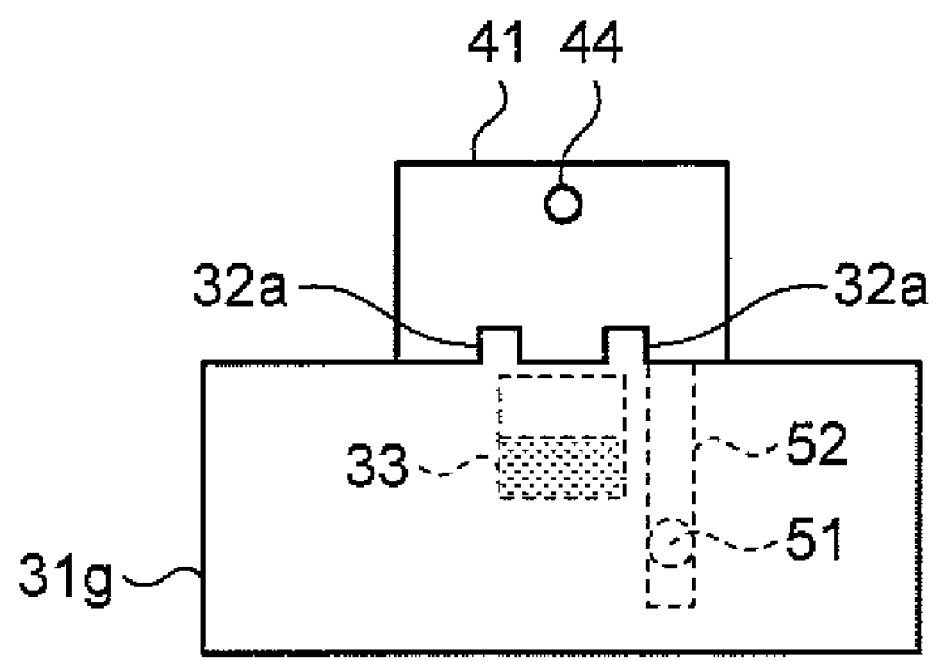
FIG. 30 is a plan view of the capsule endoscope activation system illustrated in FIG. 29 viewed in the direction of arrow D direction.

FIG. 29 is a perspective view schematically illustrating a capsule endoscope activation system according to a fifth embodiment of the present invention. FIG. 30 is a plan view of the capsule endoscope activation system illustrated in FIG. 29 viewed in the direction of arrow D.

An activation device 30g according to the fifth embodiment includes a moving member which has the above rotation shaft 51 and the shaft penetration portion 52 in a body portion 31g, and includes a control unit 61 and an input unit 62, and a shaft penetration portion 52, is jointed to a bottom portion of the rotation support portion 41 of the rotating device 40 illustrated in FIG. 23. In addition, similar to the third embodiment, a capsule endoscope 10 is fixed and supported by a support portion such that the capsule endoscope 10 and a capsule container 20 are integrally rotatable about the long axis of the capsule endoscope 10.

Further, in the body portion 31g, the rotation shaft 51 and the shaft penetration portion 52 are disposed on the outer peripheral side of guides 32a. In addition, when the width of an activation magnetic field generating unit (first activation magnetic field generating unit 33) is wider than the width of the guides 32a, the rotation shaft 51 and the shaft penetration portion 52 are disposed on the outer peripheral side of the body portion 31g with respect to the width of the activation magnetic field generating unit.

When the rotation shaft 51 is driven and the shaft penetration portion 52 moves in the extending direction of the guides 32a, it is possible to slide the rotating device 40 and place the power source of the capsule endoscope 10 in the on state in response to the above actions.

In addition, similar to the fourth embodiment, with the fifth embodiment, the control unit 61 preferably controls the moving speed of the shaft penetration portion 52 according to sliding speeds $v_1$ to $v_5$ match the above respective conditions.

Although the activation magnetic field generating unit according to the first to fifth embodiments includes a permanent magnet, an electromagnet may be used. Further, the sliding direction of the capsule container or rotating device may be opposite to the direction described with the present embodiment, and arrangement of magnetization directions of magnets does not matter as long as the magnetization directions are different between the first and second activation magnetic field generating units.

As described above, the capsule endoscope activation system according to the above embodiments is suitable to efficiently switch between on and off of a driving state of a capsule endoscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule endoscope activation system comprising:
    a capsule endoscope that includes
        a capsule-shaped casing, and
        a magnetic field detecting unit that is provided inside the capsule-shaped casing and detects a magnetic field in a direction orthogonal to a longitudinal direction of the capsule-shaped casing, the capsule endoscope being activated when the magnetic field detecting unit detects a magnetic field of a threshold or more;
    a capsule container that houses the capsule endoscope;
    a route portion in which a route is formed on which the capsule container moves on a planar face;
    an activation magnetic field generating unit that is arranged at a predetermined interval along the route, and includes a plurality of magnets for generating magnetic fields in a direction vertical to a direction in which the capsule container moves on the route, the plurality of magnets being arranged such that respective magnetization directions are different; and
    a magnetic field response unit that has a magnetization direction orthogonal respectively to a center axis direction of the longitudinal direction and a direction of the magnetic field detected by the magnetic field detecting unit.

2. The capsule endoscope activation system according to claim 1, wherein the magnetic field response unit is arranged inside the capsule endoscope.

3. The capsule endoscope activation system according to claim 1, wherein the capsule container has a first support portion for supporting the capsule endoscope rotatably about the center axis of the longitudinal direction.

4. The capsule endoscope activation system according to claim 1, wherein the capsule container has a second support portion for supporting a lateral face of the capsule endoscope.

5. The capsule endoscope activation system according to claim 4, wherein, when supporting the capsule endoscope, the second support portion is rotatable about an axis parallel to the center axis of the capsule endoscope.

6. The capsule endoscope activation system according to claim 1, wherein the plurality of magnets are arranged such that an angle formed between respective magnetization directions is 90 degrees or more.

7. The capsule endoscope activation system according to claim 1, further comprising a rotating device that includes a rotation support portion for rotatably supporting the capsule container that fixes and houses the capsule endoscope, the rotating device being movable along the route,
    wherein a rotation axis of the rotation support portion matches with the center axis of the longitudinal direction.

8. The capsule endoscope activation system according to claim 7, wherein the magnetic field response unit is arranged inside the capsule endoscope.

9. The capsule endoscope activation system according to claim 7, wherein the rotating device has a holding portion for holding the capsule container; and
    the magnetic field response unit is arranged in the holding portion.

10. The capsule endoscope activation system according to claim 1, wherein the plurality of magnets are positioned on one side of the route on a planar face containing the route.

11. The capsule endoscope activation system according to claim 1, further comprising:
    a moving member that moves the capsule container along the route; and a control unit that controls an operation of the moving member.

12. The capsule endoscope activation system according to claim 11, wherein the control unit controls a moving speed of the capsule container moved by the moving member.

13. The capsule endoscope activation system according to claim 1, wherein the capsule container has a cover made of a material which allows transmission of sterilization gas.

* * * * *